United States Patent
Shiohara et al.

(10) Patent No.: US 7,217,697 B2
(45) Date of Patent: May 15, 2007

(54) GLUCOPYRANOSYLOXYPYRAZOLE DERIVATIVE MEDICINAL COMPOSITION CONTAINING THE SAME MEDICINAL USE THEREOF AND INTERMEDIATE THEREFOR

(75) Inventors: Hiroaki Shiohara, Nagano (JP); Hideki Fujikura, Nagano (JP); Nobuhiko Fushimi, Nagano (JP); Fumiaki Ito, Nagano (JP); Masayuki Isaji, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 10/479,083

(22) PCT Filed: May 27, 2002

(86) PCT No.: PCT/JP02/05093

§ 371 (c)(1),
(2), (4) Date: May 6, 2004

(87) PCT Pub. No.: WO02/098893

PCT Pub. Date: Dec. 12, 2002

(65) Prior Publication Data

US 2004/0176308 A1 Sep. 9, 2004

(30) Foreign Application Priority Data

May 30, 2001 (JP) .............................. 2001-163382

(51) Int. Cl.
*A01N 43/04* (2006.01)
*A61K 31/70* (2006.01)
*C07H 15/00* (2006.01)
*C07H 17/00* (2006.01)

(52) U.S. Cl. ...................... 514/25; 514/27; 536/4.1; 536/17.2; 536/17.3; 536/17.4; 536/18.1

(58) Field of Classification Search ................. 514/25, 514/27; 536/4.1, 17.2, 17.3, 17.4, 18.1
See application file for complete search history.

(56) References Cited

U.S. PATENT DOCUMENTS 6,972,283 B2 * 12/2005 Fujikura et al. .............. 514/27

FOREIGN PATENT DOCUMENTS

| EP | 1213296 A1 | 6/2002 |
|---|---|---|
| WO | WO01/16147 A1 | 3/2001 |
| WO | WO01/32637 A1 | 5/2001 |
| WO | WO01/34579 A1 | 5/2001 |
| WO | WO02/36602 A1 | 5/2002 |
| WO | WO02053573 A1 | 7/2002 |
| WO | WO02068439 A1 | 9/2002 |
| WO | WO02068440 A1 | 9/2002 |
| WO | WO02088157 A1 | 11/2002 |

OTHER PUBLICATIONS

Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996.*
Kenji Tsujihara, et al.; Na+-Glucose Cotransporter (SGLT) Inhibitors as Antidiabetic Agents. 4. Synthesis and Pharmacological Properties of 4'-Dehydroxyphlorizin Derivatives Substituted on the B Ring; J. Med. Chem 1999, 42, 5311-5324.
Bryan Mackensie, et al.; Biophysical Characteristics of the Pig Kidney Na+/Glucose Cotransporter SGLT2 Reveal a Common Mechanism for SGLT1 and SGLT2; The Journal of Biological Chemistry; vol. 271, No. 51, Issue of Dec. 20, pp. 32678-32683, 1996.

* cited by examiner

*Primary Examiner*—Shaojia Anna Jiang
*Assistant Examiner*—Traviss McIntosh
(74) *Attorney, Agent, or Firm*—Sughrue Mion, PLLC

(57) ABSTRACT

The present invention provides glucopyranosyloxypyrazole derivatives represented by the general formula:

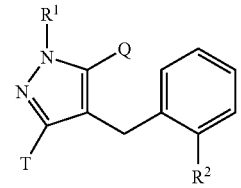

(I)

wherein $R^1$ is a hydrogen atom or a hydroxyalkyl group; one of Q and T is a group represented by the general formula;

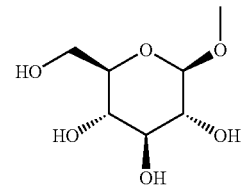

the other is an optionally substituted alkyl group or a cycloalkyl group; and $R^2$ is a halogen atom, a hydroxy group, an optionally substituted alkyl group, an optionally substituted alkoxy group, an alkylthio group, a group of the general formula: -A-$R^3$ wherein A is a single bond, an oxygen atom, a methylene group, an ethylene group, —$OCH_2$— or —$CH_2O$—; and $R^3$ is a cycloalkyl group, a heterocycloalkyl group, an optionally substituted aryl group, an optionally substituted tiazolyl group or an optionally substituted pyridyl group, pharmaceutically acceptable salts thereof or prodrugs thereof, which exert an excellent inhibitory activity in human SGLT1, and therefore are useful as drugs for the prevention or treatment of a disease associated with hyperglycemia such as diabetes, diabetic complications or obesity, pharmaceutical compositions comprising the same, pharmaceutical uses thereof and production intermediates thereof.

5 Claims, No Drawings

GLUCOPYRANOSYLOXYPYRAZOLE DERIVATIVE MEDICINAL COMPOSITION CONTAINING THE SAME MEDICINAL USE THEREOF AND INTERMEDIATE THEREFOR

TECHNICAL FIELD

The present invention relates to glucopyranosyloxypyrazole derivatives, pharmaceutically acceptable salts thereof or prodrugs thereof which are useful as medicaments, pharmaceutical compositions containing the same, pharmaceutical uses thereof and production intermediates thereof.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed.

In recent years, development of various antidiabetic agents has been progressing with the background of a rapid increase of diabetic patients. For example, α-glucosidase inhibitors, which delay carbohydrate digestion and absorption at the small intestine, are used to improve postprandial hyperglycemia. However, since α-glucosidase inhibitors do not affect elevated blood glucose levels after ingesting glucose, which is one of monosaccharides (Journal of Japanese Society of Nutrition and Food Science, vol. 45, page 27, 1992), with recently changing components of carbohydrates in meals, it has been desired to develop agents which exert a wider range of activities inhibiting carbohydrate absorption.

In the meantime, it has been known that SGLT1, sodium-dependent glucose transporter 1, exists in the small intestine which controls carbohydrates absorption. It has also been reported that insufficiency of glucose and galactose absorption arises in patients with dysfunction due to congenital abnormalities of human SGLT1 (Supplementary Volume of Nippon Rinsho, Ryoikibetsu Shokogun 19, pages 555–556; Saishin Igaku, vol. 51, pages 84–90, 1996; Nippon Rinsho, vol. 55, no. 8, pages 249–257, 1997). In addition, it has been confirmed that SGLT1 relates to glucose and galactose absorption (Kidney and Dialysis, extra edition, pages 232–237, 1998; Nature, vol. 350, pages 354–456, 1991).

Furthermore, generally in diabetic patients, carbohydrate digestion and absorption are accelerated. For example, it is confirmed that mRNA and protein of SGLT1 increase and absorption of glucoses are accelerated in OLETF rats and Wistar-rats with streptozotocin-induced diabetic symptoms (Diabetologia, vol. 41, pages 1459–1466, 1998; Biochemical Society Transactions, vol. 25, page 479S, 1997).

Therefore, blocking a human SGLT1 activity inhibits absorption of carbohydrates such as glucose at the small intestine, subsequently can prevent increase of blood glucose level. Especially, it is considered that delaying carbohydrate absorption based on the above mentioned mechanism is effective to normalize postprandial hyperglycemia. In addition, since increase of SGLT1 in the small intestine is thought to contribute to increased carbohydrate absorption in diabetic patients, fast development of agents which have a potent inhibitory activity in human SGLT1 has been desired for preventing or treating diabetes.

DISCLOSURE OF THE INVENTION

The present inventors have studied earnestly to find compounds exhibiting an inhibitory activity in human SGLT1. As a result, it was found that certain glucopyranosyloxypyrazole derivatives represented by the following general formula (I) show an inhibitory activity in human SGLT1 at the small intestine and exert an excellent inhibitory activity in increase of blood glucose level as shown below, thereby forming the basis of the present invention.

The present invention is to provide novel compounds which exert an excellent inhibitory activity of blood glucose level increase by exhibiting an inhibitory activity in human SGLT1 and inhibiting absorption of carbohydrate such as glucose at the small intestine.

This is, the present invention relates to a glucopyranosyloxypyrazole derivative represented by the general formula:

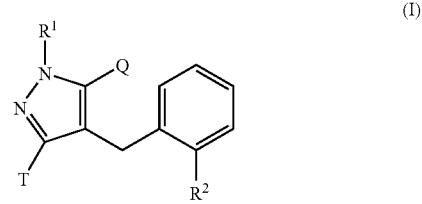

wherein $R^1$ is a hydrogen atom or a hydroxy($C_{2-6}$ alkyl) group; one of Q and T is a group represented by the general formula;

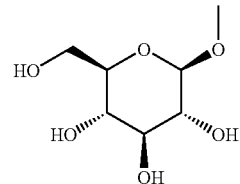

the other is a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group; and $R^2$ is a halogen atom, a hydroxy group, a $C_{1-6}$ alkyl group, a $C_{1-6}$ alkoxy group, a $C_{1-6}$ alkylthio group, a halo($C_{1-6}$ alkyl) group, a halo($C_{1-6}$ alkoxy) group, a $C_{1-6}$alkoxy-substituted ($C_{1-6}$ alkoxy) group, a $C_{3-7}$ cycloalkyl-substituted ($C_{2-6}$ alkoxy) group, or a group of the general formula: -A-$R^3$ wherein A is a single bond, an oxygen atom, a methylene group, an ethylene group, —OCH$_2$— or —CH$_2$O—; and $R_3$ is a $C_{3-7}$ cycloalkyl group, a $C_{3-7}$ heterocycloalkyl group, an aryl group which may have 1–3 the same or different substituents selected from a halogen atom, a hydroxy group, an amino group, a $C_{1-6}$ alkyl group, a $C_{1-6}$ alkoxy group, a $C_{2-6}$ alkenyloxy group, a halo($C_{1-6}$ alkyl) group, a hydroxy($C_{1-6}$ alkyl) group, a carboxy group, a $C_{2-7}$ alkoxycarbonyl group, a cyano group and a nitro group, a thiazolyl group which may have a substituent selected from a halogen atom and a $C_{1-6}$ alkyl group, or a pyridyl group which may have a substituent selected from a halogen atom and a $C_{1-6}$ alkyl group, a pharmaceutically acceptable salt thereof or a prodrug thereof.

Also, the present invention relates to a pharmaceutical composition, a human SGLT1 inhibitor and an agent for the prevention or treatment of a disease associated with hyperglycemia, which comprise as an active ingredient a glucopyranosyloxypyrazole derivative represented by the above general formula (I), a pharmaceutically acceptable salt thereof or a prodrug thereof.

The present invention relates to a method for the prevention or treatment of a disease associated with hyperglycemia, which comprises administering an effective amount of a glucopyranosyloxypyrazole derivative represented by the above general formula (I), a pharmaceutically acceptable salt thereof or a prodrug thereof.

The present invention relates to a use of a glucopyranosyloxypyrazole derivative represented by the above general formula (I), a pharmaceutically acceptable salt thereof or a prodrug thereof for the manufacture of a pharmaceutical composition for the prevention or treatment of a disease associated with hyperglycemia.

The present invention relates to a pharmaceutical combination which comprises (A) a glucopyranosyloxypyrazole derivative represented by the above general formula (I), a pharmaceutically acceptable salt thereof or a prodrug thereof, and (B) at least one member selected from the group consisting of an insulin sensitivity enhancer, a glucose absorption inhibitor, a biguanide, an insulin secretion enhancer, a SGLT2 inhibitor, insulin, an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a $\beta_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blockade, a centrally acting antihypertensive agent, an $\alpha_2$-adrenoceptor agonist, an antiplatelets agent, a uric acid synthesis inhibitor, a uricosuric agent and a urinary alkalinizer.

The present invention relates to a method for the prevention or treatment of a disease associated with hyperglycemia, which comprises administering an effective amount of (A) a glucopyranosyloxypyrazole derivative represented by the above general formula (I), a pharmaceutically acceptable salt thereof or a prodrug thereof, in combination with (B) at least one member selected from the group consisting of an insulin sensitivity enhancer, a glucose absorption inhibitor, a biguanide, an insulin secretion enhancer, a SGLT2 inhibitor, insulin, an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a $\beta_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blockade, a centrally acting antihypertensive agent, an $\alpha_2$-adrenoceptor agonist, an antiplatelets agent, a uric acid synthesis inhibitor, a uricosuric agent and a urinary alkalinizer.

The present invention relates to a use of (A) a glucopyranosyloxypyrazole derivative represented by the above general formula (I), a pharmaceutically acceptable salt thereof or a prodrug thereof, and (B) at least one member selected from the group consisting of an insulin sensitivity enhancer, a glucose absorption inhibitor, a biguanide, an insulin secretion enhancer, a SGLT2 inhibitor, insulin, an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethylglutaryl coenzyme A reductase inhibitor, a fibric acid derivative, a $\beta_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blockade, a centrally acting antihypertensive agent, an $\alpha_2$-adrenoceptor agonist, an antiplatelets agent, a uric acid synthesis inhibitor, a uricosuric agent and a urinary alkalinizer, for the manufacture of a pharmaceutical composition for the prevention or treatment of a disease associated with hyperglycemia.

Furthermore, the present invention relates to a glucopyranosyloxypyrazole derivative represented by the general formula:

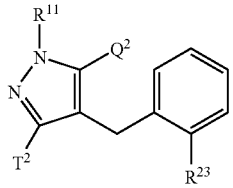

(II)

wherein $R^{11}$ is a hydrogen atom or an optionally protected hydroxy ($C_{2-6}$ alkyl) group; one of $Q^2$ and $T^2$ is a 2,3,4,6-tetra-O-acetyl-β-D-glucopyranosyloxy group and the other is a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group; and $R^{23}$ is a halogen atom, an optionally protected hydroxy group, a $C_{1-6}$ alkyl group, a $C_{1-6}$ alkoxy group, a $C_{1-6}$ alkylthio group, a halo($C_{1-6}$ alkyl) group, a halo($C_{1-6}$ alkoxy) group, a $C_{1-6}$alkoxy-substituted ($C_{1-6}$ alkoxy) group, a $C_{3-7}$ cycloalkyl-substituted ($C_{2-6}$ alkoxy) group or a group of the general formula: -A-$R^{32}$ wherein A is a single bond, an oxygen atom, a methylene group, an ethylene group, —OCH$_2$— or —CH$_2$O—; and $R^{32}$ is a $C_{3-7}$ cycloalkyl group, a $C_{3-7}$ heterocycloalkyl group, an aryl group which may have 1–3 the same or different substituents selected from a halogen atom, an optionally protected hydroxy group, an optionally protected amino group, a $C_{1-6}$ alkyl group, a $C_{1-6}$ alkoxy group, a $C_{2-6}$ alkenyloxy group, a halo($C_{1-6}$ alkyl) group, an optionally protected hydroxy($C_{1-6}$ alkyl) group, an optionally protected carboxy group, a $C_{2-7}$ alkoxycarbonyl group, a cyano group and a nitro group, a thiazolyl group which may have a substituent selected from a halogen atom and a $C_{1-6}$ alkyl group, or a pyridyl group which may have a substituent selected from a halogen atom and a $C_{1-6}$ alkyl group, or a salt thereof, and a glucopyranosyloxypyrazole derivative represented by the general formula:

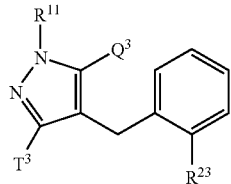

(III)

wherein $R^{11}$ is a hydrogen atom or an optionally protected hydroxy ($C_{2-6}$ alkyl) group; one of $Q^3$ and $T^3$ is a hydroxy group and the other is a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group; and $R^{23}$ is a halogen atom, an optionally protected hydroxy group, a $C_{1-6}$ alkyl group, a $C_{1-6}$ alkoxy group, a $C_{1-6}$ alkylthio group, a halo($C_{1-6}$ alkyl) group, a halo($C_{1-6}$ alkoxy) group, a $C_{1-6}$ alkoxy-substituted ($C_{1-6}$ alkoxy) group, a $C_{3-7}$ cycloalkyl-substituted ($C_{2-6}$ alkoxy) group or a group of the general formula: -A-$R^{32}$ wherein A is a single bond, an oxygen atom, a methylene group, an ethylene group, —OCH$_2$— or —CH$_2$O—; and $R^{32}$ is a $C_{3-7}$ cycloalkyl group, a $C_{3-7}$ heterocycloalkyl group, an aryl group which may have 1–3 the same or different substituents selected from a halogen atom, an optionally protected hydroxy group, an optionally protected amino group, a $C_{1-6}$ alkyl group, a $C_{1-6}$ alkoxy group, a $C_{2-6}$ alkenyloxy group, a halo($C_{1-6}$ alkyl) group, an optionally protected hydroxy ($C_{1-16}$ alkyl) group, an optionally protected carboxy group, a $C_{2-7}$ alkoxycarbonyl group, a cyano group and a nitro group, a thiazolyl group which may have a substituent selected from a halogen atom and a $C_{1-6}$ alkyl group, or a pyridyl group which may have a substituent selected from a halogen atom and a $C_{1-6}$ alkyl group, or a salt thereof.

In the present invention, the term "$C_{1-6}$ alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "hydroxy($C_{1-6}$ alkyl) group" means the above $C_{1-6}$ alkyl group substituted by a hydroxy group; the term "$C_{2-6}$ alkyl group" means a straight-chained or branched alkyl group having 2 to 6 carbon atoms such as an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; and the term "hydroxy($C_{2-6}$ alkyl) group" means the above $C_{2-6}$ alkyl group substituted by a hydroxy group such as 2-hydroxyethyl group, 3-hydroxypropyl group or the like. The term "$C_{1-6}$ alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; the term "$C_{1-6}$ alkoxy-substituted ($C_{1-6}$ alkyl) group" means the above $C_{1-6}$ alkyl group substituted by the above $C_{1-6}$ alkoxy group; the term "$C_{1-6}$ alkoxy-substituted ($C_{1-6}$ alkoxy) group" means the above $C_{1-6}$ alkoxy group substituted by the above $C_{1-6}$ alkoxy group such as a methoxymethoxy group or the like; and the term "$C_{2-6}$ alkenyloxy group" means the above $C_{1-6}$ alkoxy group except for a methoxy group, having an unsaturated bond such as an allyloxy group or the like; the term "$C_{1-6}$ alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like. The term "$C_{3-7}$ cycloalkyl group" means a cyclopropyl group, a cyclobutyl group, a cyclopentyl group, a cyclohexyl group or a cycloheptyl group. The term "$C_{3-7}$ cycloalkyl-substituted ($C_{2-6}$ alkoxy) group" means the above $C_{1-6}$ alkoxy group except for a methoxy group, substituted by the above $C_{3-7}$ cycloalkyl group; and the term "$C_{3-7}$ heterocycloalkyl group" means the above $C_{3-7}$ cycloalkyl group which contains 1 to 3 the same or different hetero atoms selected from an oxygen atom, a sulfur atom and a nitrogen atom in the ring such as a 4-tetrahydropyranyl group or the like. The term "halogen atom" means a fluorine atom, a chlorine atom, a bromine atom or an iodine atom; the term "halo($C_{1-6}$ alkyl) group" means the above $C_{1-6}$ alkyl group substituted by 1 to 5 the same or different halogen atoms defined above, such as trifluoromethyl group, a pentafluoroethyl group or the like; and the term "halo($C_{1-6}$ alkoxy) group" means the above $C_{1-6}$ alkoxy group substituted by 1 to 5 the same or different halogen atoms defined above. The term "$C_{2-7}$ alkoxycarbonyl group" means a straight-chained or branched alkoxycarbonyl group having 2 to 7 carbon atoms such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a hexyloxycarbonyl group or the like; and the term "aryl group" means mono- to tricyclic aromatic hydrocarbon group such as a phenyl group, a naphthyl group, or the like. The term "hydroxy-protective group" means a hydroxy-protective group used in general organic syntheses such as a benzyl group, a methoxymethyl group, an acetyl group, a tert-butyldimethylsilyl group, an allyl group, or the like; the term "amino-protective group" means an amino-protective group used in general organic syntheses such, as a benzyloxycarbonyl group, a tert-butoxycarbonyl group, a benzyl group, a trifluoroacetyl group, or the like; and the term "carboxy-protective group" means a carboxy-protective group used in general organic syntheses such as a benzyl group, a tert-butyldimethylsilyl group, an allyl group, or the like.

For example, the above general formula (I) of the present invention can be prepared according to the following procedure:

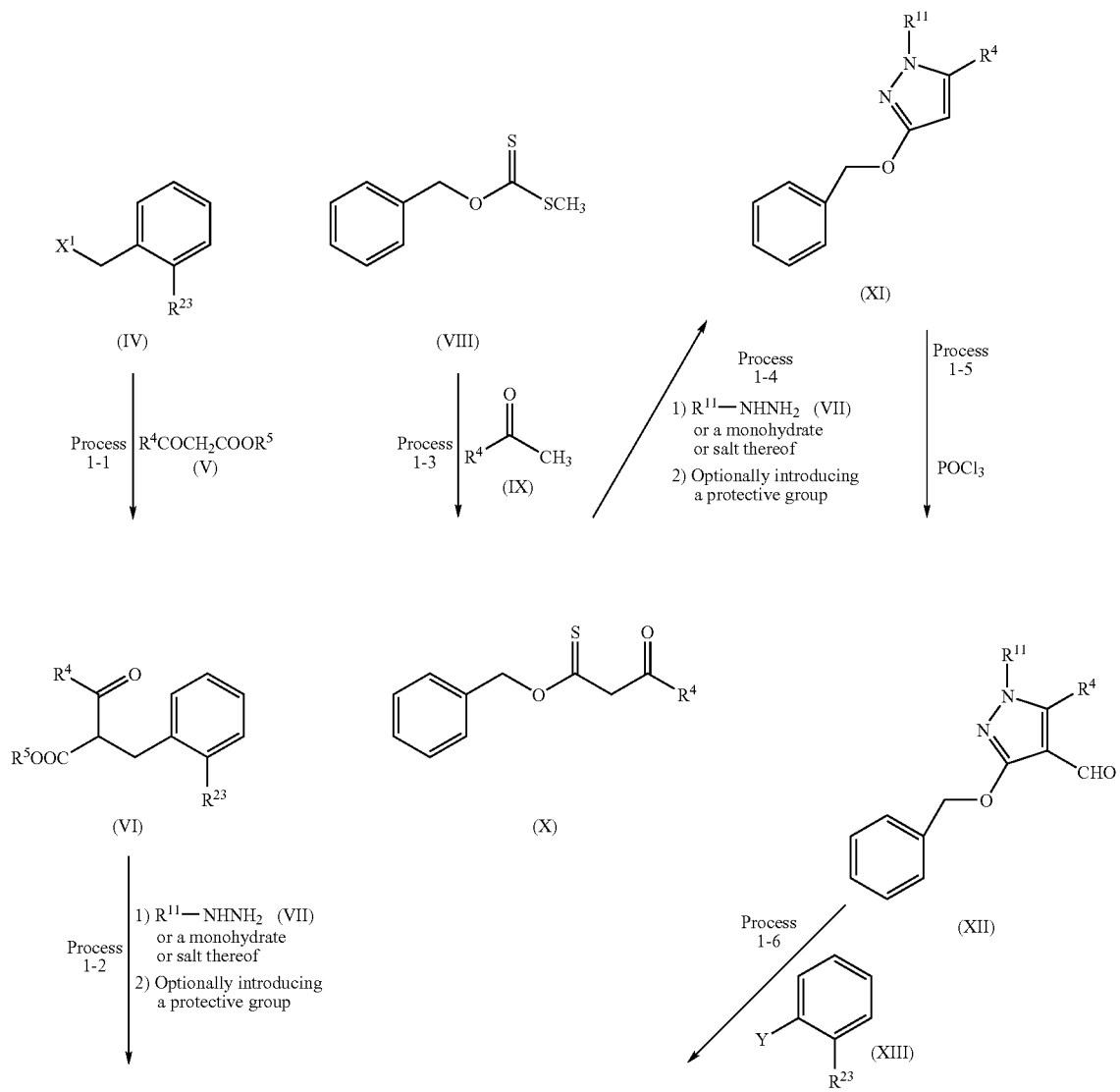

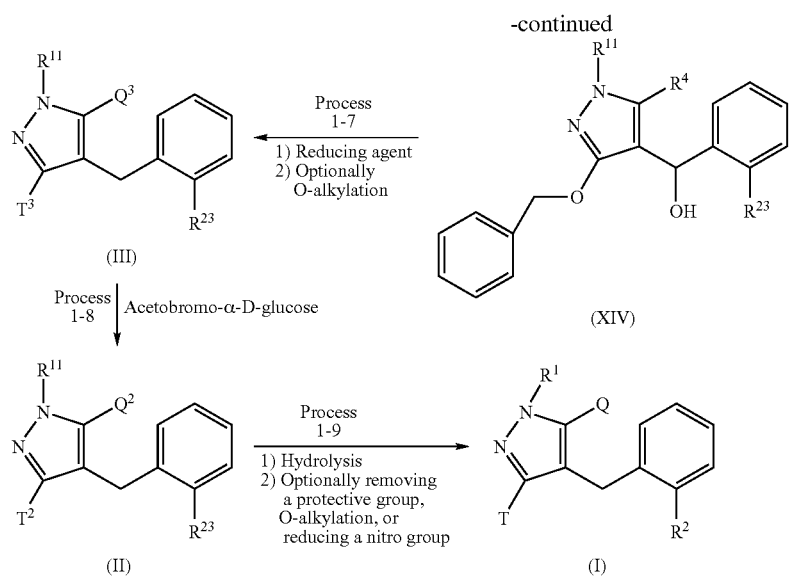

wherein $X^1$ represents a leaving group such as a halogen atom, a mesyloxy group, a tosyloxy group, or the like; Y represents MgBr, MgCl, MgI, or a lithium atom; $R^4$ represents a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group; $R^5$ represents a $C_{1-6}$ alkyl group; and $R^1$, $R^2$, $R^{11}$, $R^{23}$, Q, $Q^2$, $Q^3$, T, $T^2$ and $T^3$ have the same meanings as defined above.

Process 1-1

A compound represented by the above general formula (VI) can be prepared by condensing a benzyl compound represented by the above general formula (IV) with a ketoacetate ester compound represented by the above general formula (V) in the presence of a base such as sodium hydride, potassium tert-butoxide or the like in an inert solvent. As the inert solvent used in the reaction, for example, 1,2-dimethoxyethane, tetrahydrofuran, N,N-dimethylformamide, a mixed solvent thereof and the like can be illustrated. The reaction temperature is usually from room temperature to reflux temperature, and the reaction time is usually from 1 hour to 1 day, varying based on a used starting material, solvent and reaction temperature.

Process 1-2

A benzylpyrazole derivative of the present invention represented by the above general formula (III) can be prepared by condensing a compound represented by the above general formula (VI) with a hydrazine compound represented by the above general formula (VII), its monohydrate or a salt thereof in the presence or absence of a base in an inert solvent and then optionally introducing a protective group to its hydroxy group in the usual way. As the inert solvent used in the condensation, for example, toluene, tetrahydrofuran, chloroform, methanol, ethanol, a mixed solvent thereof and the like can be illustrated. As the base, for example, triethylamine, diisopropylethylamine, pyridine, sodium methoxide, sodium ethoxide and the like can be illustrated. The reaction temperature is usually from room temperature to reflux temperature, and the reaction time is usually from 1 hour to 1 day, varying based on a used starting material, solvent and reaction temperature. The obtained benzylpyrazole derivative represented by the above general formula (III) can be also used in the following process suitably after being converted into a salt thereof in the usual way.

Process 1-3

A compound represented by the above general formula (X) can be prepared by condensing a dithiocarbonate ester compound represented by the above general formula (VIII) with a ketone compound represented by the above general formula (IX) in the presence of a base such as sodium amide in an inert solvent. As the inert solvent used in the reaction, toluene and the like can be illustrated. The reaction temperature is usually from −20° C. to room temperature, and the reaction time is usually from 30 minutes to 1 day, varying based on a used starting material, solvent and reaction temperature.

Process 1-4

A beyzyloxypyrazole derivative represented by the above general formula (XI) can be prepared by condensing a compound represented by the above general formula (X) with a hydrazine compound represented by the above general formula (VII), its monohydrate or a salt thereof in the presence of a base such as triethylamine, diisopropylethylamine or the like in an inert solvent, and then optionally introducing a protective group to its hydroxy group in the usual way. As the inert solvent used in the condensation, acetonitrile and the like can be illustrated. The reaction temperature is usually from 0° C. to reflux temperature, and the reaction time is usually from 1 hour to 1 day, varying based on a used starting material, solvent and reaction temperature.

Process 1-5

A pyrazolealdehyde derivative represented by the above general formula (XII) can be prepared by subjecting a compound represented by the above general formula (XI) to Vilsmeier reaction using phosphorus oxychloride and N,N-dimethylformamide in a various solvent. As the solvent used in the reaction, for example, N,N-dimethylformamide and the like can be illustrated. The reaction temperature is usually from 0° C. to reflux temperature, and the reaction time is usually from 30 minutes to 1 day, varying based on a used starting material, solvent and reaction temperature.

Process 1-6

A compound represented by the above general formula (XIV) can be prepared by condensing a compound represented by the above general formula (XII) with a Grignard reagent or a lithium reagent represented by the above general formula (XIII) in an inert solvent. As the inert solvent used in the reaction, tetrahydrofuran, diethyl ether, a mixed solvent thereof and the like can be illustrated. The reaction temperature is usually from −78° C. to room temperature, and the reaction time is usually from 30 minutes to 1 day, varying based on a used starting material, solvent and reaction temperature.

Process 1-7

A benzylpyrazole derivative of the present invention represented by the above general formula (III) can be prepared by subjecting a compound represented by the above general formula (XIV) to catalytic hydrogenation using a palladium catalyst such as palladium-carbon powder in the presence or absence of an acid such as hydrochloric acid in an inert solvent, and in a case of a compound having any sulfur atom represented by the above general formula (XIV), optionally subjecting the resulting compound to acid treatment in an aqueous solution of trifluoroacetic acid and dimethyl sulfide usually at 0° C. to reflux temperature for 30 minutes to 1 day. As the solvent used in the catalytic hydrogenation, for example, methanol, ethanol, tetrahydrofuran, ethyl acetate, acetic acid, isopropanol, a mixed solvent thereof and the like can be illustrated. The reaction temperature is usually from room temperature to reflux temperature, and the reaction time is usually from 30 minutes to 1 day, varying based on a used starting material, solvent and reaction temperature. In a case that $R^{23}$ is converted into a hydroxy group by the above catalytic hydrogenation, the eliminated substituent can be introduced according to a similar manner to the following Process 4. The obtained benzylpyrazole derivative represented by the above general formula (III) can be also used in the following process suitably after being converted into a salt thereof in the usual way.

Process 1-8

1) In case that one of $Q^3$ and $T^3$ is a $C_{1-6}$ alkyl group, a $C_{1-6}$ alkoxy-substituted ($C_{1-6}$ alkyl) group or a $C_{3-7}$ cycloalkyl group in a benzylpyrazole derivative represented by the above general formula (III), a corresponding compound of the present invention represented by the above general formula (II) can be prepared by subjecting a corresponding benzylpyrazole derivative represented by the above general formula (III) to glucosidation using acetobromo-α-D-glucose in the presence of a base such as silver carbonate, sodium hydrate or the like in an inert solvent. As the inert solvent used in the reaction, for example, tetrahydrofuran, dimethoxyethane, N,N-dimethylformamide, a mixed solvent thereof and the like can be illustrated. The reaction temperature is usually from room temperature to reflux temperature, and the reaction time is usually from 1 hour to 1 day, varying based on a used starting material, solvent and reaction temperature.

2) In case that one of $Q^3$ and $T^3$ is a halo($C_{1-6}$ alkyl) group in a benzylpyrazole derivative represented by the above general formula (III), a corresponding compound of the present invention represented by the above general formula (II) can be prepared by subjecting a corresponding benzylpyrazole derivative represented by the above general formula (III) to glucosidation using acetobromo-α-D-glucose in the presence of a base such as potassium carbonate or the like in an inert solvent. As the inert solvent used in the reaction, for example, tetrahydrofuran, acetonitrile, a mixed solvent thereof and the like can be illustrated. The reaction temperature is usually from room temperature to reflux temperature, and the reaction time is usually from 1 hour to 1 day, varying based on a used starting material, solvent and reaction temperature.

3) In case that one of $Q^3$ and $T^3$ is a $C_{2-6}$ alkyl group, a $C_{1-6}$ alkoxy-substituted ($C_{1-6}$ alkyl) group or a $C_{3-7}$ cycloalkyl group in a benzylpyrazole derivative represented by the above general formula (III), a corresponding compound of the present invention represented by the above general formula (II) can be also prepared by subjecting a corresponding benzylpyrazole derivative represented by the above general formula (III) to glucosidation using acetobromo-α-D-glucose in the presence of a base such as sodium hydroxide, potassium hydroxide, potassium carbonate or the like and a phase transfer catalyst such as benzyltri(n-butyl) ammonium chloride, benzyltri(n-butyl)-ammonium bromide, tetra(n-butyl)ammonium hydrogen sulfate or the like in a water-containing inert solvent. As the inert solvent used in the reaction, dichloromethane, toluene, benzo-trifluoride, a mixed solvent thereof and the like can be illustrated. The reaction temperature is usually from 0° C. to reflux temperature, and the reaction time is usually from 30 minutes to 1 day, varying based on a used starting material, solvent and reaction temperature.

The obtained glucosidated benzylpyrazole derivative represented by the above general formula (II) can be also used in the following process suitably after being converted into a salt thereof and separated in the usual way.

Process 1-9

A glucopyranosyloxypyrazole derivative of the present invention represented by the above general formula (I) can be prepared by subjecting a compound represented by the above general formula (II) to alkaline hydrolysis and optionally removal of the protective group, O-alkylation or reduction of the nitro group. As the solvent used in the hydrolysis reaction, for example, methanol, ethanol, tetrahydrofuran, water, a mixed solvent thereof and the like can be illustrated. As the base, sodium hydroxide, sodium methoxide, sodium ethoxide and the like can be illustrated. The reaction temperature is usually from 0° C. to reflux temperature, and the reaction time is usually from 30 minutes to 1 day, varying based on a used starting material, solvent and reaction temperature. As mentioned above, in case that a compound has a protective group at $R^{23}$ after the hydrolysis, the protective group can be removed by suitably treating in the usual way. In addition, in case that $R^{23}$ is converted into a hydroxy group by the catalytic reduction described in Process 1-7, an eliminated substituent can be introduced in a similar manner to the following Process 4. Furthermore, a compound having a nitro group at $R^2$ represented by the above general formula (I) can be also derived into a corresponding compound having an amino group by catalytic reduction in an inert solvent such as ethyl acetate using a platinum catalyst such as platinum oxide or the like at usually from room temperature to reflux temperature and usually from 30 minutes to 1 day in the usual way after completing the above reaction.

Among the compounds represented by the above general formula (III) of the present invention as starting materials, there can be the following three tautomers in a compound having a hydrogen atom at $R^{11}$, varying based on difference in the reaction conditions. The compounds represented by the above general formula (III) of the present invention include all compounds:

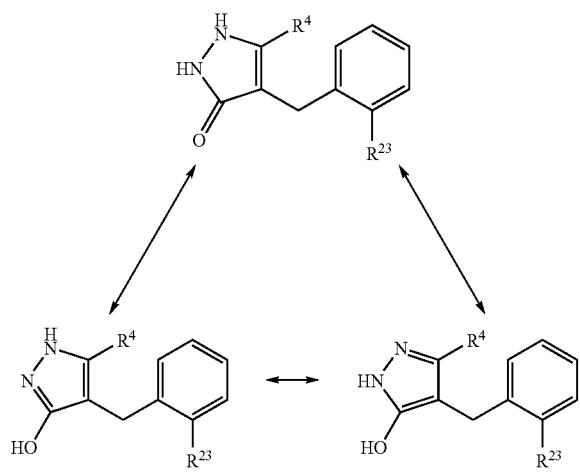

wherein $R^4$ and $R^{23}$ have the same meanings as defined above.

Among the compounds represented by the above general formula (I), a compound wherein $R^1$ represents a hydroxy ($C_{2-6}$ alkyl) group, for example, can be also prepared according to the following procedures:

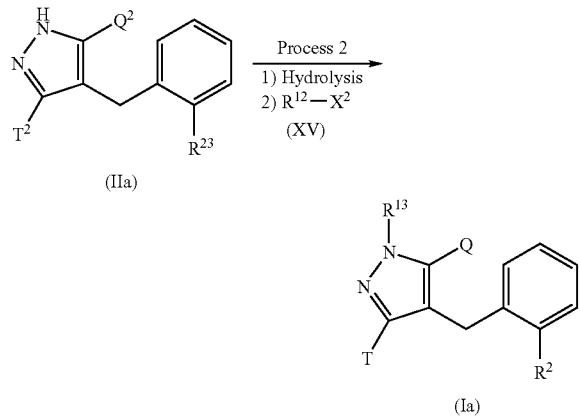

wherein $X^2$ represents a leaving group such as a halogen atom, a mesyloxy group, a tosyloxy group or the like; $R^{12}$ represents a hydroxy($C_{2-6}$ alkyl) group which may have a protective group; $R^{13}$ represents a hydroxy($C_{2-6}$ alkyl) group; and $R^2$, $R^{23}$, Q, $Q^2$, T and $T^2$ have the same meanings as defined above.

Process 2

A glucopyranosyloxypyrazole derivative represented by the above general formula (Ia) of the present invention can be prepared by hydrolyzing a compound represented by the above general formula (IIa) in a similar manner to that described in the above Process 1-9 and then by subjecting the resulting compound to N-alkylation using an alkylating agent represented by the above general formula (XV) in an inert solvent in the presence of a base such as cesium carbonate, potassium carbonate or the like and optionally a catalytic amount of sodium iodide. In case of a compound having a protective group thereafter, a glucopyranosyloxy-pyrazole derivative represented by the above general formula (Ia) of the present invention can be prepared successively by suitably removing the protective group in the usual way as occasion demands. As the solvent used in the N-alkylation, acetonitrile, ethanol, 1,2-dimethoxyethane, tetrahydrofuran, N,N-dimethylformamide, dimethylsulfoxide, a mixed solvent thereof and the like can be illustrated. The reaction temperature is usually from room temperature to reflux temperature, and the reaction time is usually from 10 minutes to 1 day, varying based on a used starting material, solvent and reaction temperature.

Among the compounds represented by the above general formula (I), a compound wherein $R^2$ represents a hydroxy group, for example, can be also prepared according to the following procedures:

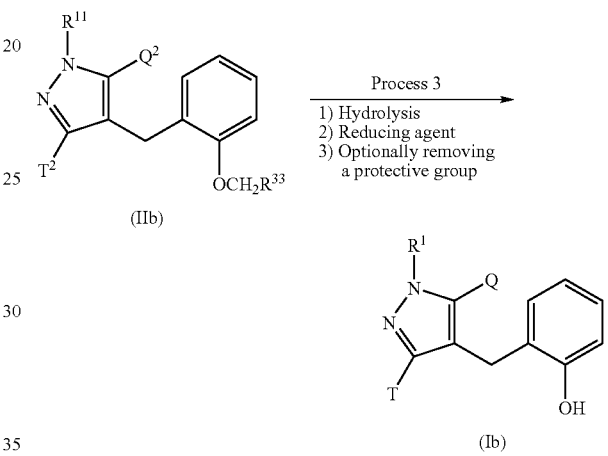

wherein $R^{33}$ represents an aryl group which may have 1–3 substituents selected from a halogen atom, an optionally protected hydroxy group, an optionally protected amino group, a $C_{1-6}$ alkyl group, a $C_{1-6}$ alkoxy group, a $C_{2-6}$ alkenyloxy group, a halo($C_{1-6}$ alkyl) group, an optionally protected hydroxy-substituted ($C_{1-6}$ alkyl) group, an optionally protected carboxy group, a $C_{2-7}$ alkoxycarbonyl group, a cyano group and a nitro group; and $R^1$, $R^{11}$, Q and T have the same meanings as defined above.

Process 3

A glucopyranosyloxypyrazole derivative represented by the above general formula (Ib) of the present invention can be prepared by hydrolyzing a compound represented by the above general formula (IIb) in a similar manner to that described in the above Process 1-9, then by subjecting the resulting compound to catalytic hydrogenation using a palladium catalyst such as palladium-carbon powder in an inert solvent and successively by suitably removing the protective group in the usual way as occasion demands. As the solvent used in the catalytic hydrogenation, methanol, ethanol, tetrahydrofuran, ethyl acetate, acetic acid, isopropanol, a mixed solvent thereof and the like can be illustrated. The reaction temperature is usually from room temperature to reflux temperature, and the reaction time is usually from 10 minutes to 1 day, varying based on a used starting material, solvent and reaction temperature.

Among the compounds represented by the above general formula (I) of the present invention, a compound wherein $R^2$ represents a group of the general formula: —$OCH_2R^{34}$ or —OR³⁴ in which R³⁴ represents an aryl group which may have 1–3 substituents selected from a halogen atom, a hydroxy group, an amino group, a $C_{1-6}$ alkyl group, a $C_{1-6}$ alkoxy group, a $C_{2-6}$ alkenyloxy group, a halo($C_{1-6}$ alkyl) group, a hydroxy($C_{1-6}$ alkyl) group, a carboxy group, a $C_{2-7}$ alkoxycarbonyl group, a cyano group and a nitro group, for example, can be also prepared according to the following procedures:

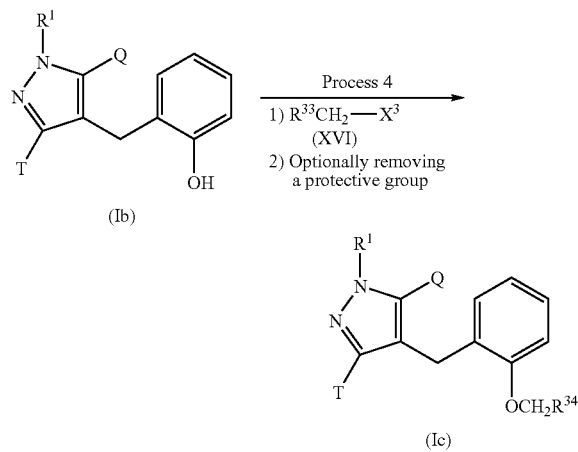

wherein $X^3$ represents a leaving group such as a halogen atom, a mesyloxy group, a tosyloxy group or the like; and $R^1$, $R^{33}$, $R^{34}$, Q and T have the same meanings as defined above.

Process 4

A glucopyranosyloxypyrazole derivative represented by the above general formula (Ic) of the present invention can be prepared by subjecting a glucopyranosyloxypyrazole derivative represented by the above general formula (Ib) to O-alkylation using an alkylating agent represented by the above general formula (XVI) in an inert solvent in the presence of a base such as cesium carbonate, potassium carbonate, sodium hydroxide, diisopropylethylamine or the like. In case of a compound having a protective group thereafter, a glucopyranosyloxypyrazole derivative represented by the above general formula (Ic) of the present invention can be prepared successively by suitably removing the protective group in the usual way. As the solvent used in the O-alkylation, acetonitrile, ethanol, 1,2-dimethoxyethane, tetrahydrofuran, N,N-dimethylformamide, acetone, a mixed solvent thereof and the like can be illustrated. The reaction temperature is usually from 0° C. to reflux temperature, and the reaction time is usually from 1 hour to 1 day, varying based on a used starting material, solvent and reaction temperature.

wherein $R^1$, $R^{11}$, $R^{33}$, $R^{34}$, Q, $Q^2$, T and $T^2$ have the same meanings as defined above.

Process 5

A glucopyranosyloxypyrazole derivative represented by the above general formula (Id) of the present invention can be prepared by condensing a glycosylated benzylpyrazole derivative represented by the above general formula (IIc) with a perchlorate, a fluoborate or a hexafluorophosphate of a compound represented by the above general formula (XVII) in the presence of copper and a base such as triethylamine in an inert solvent, and then by treating a resulting compound in a similar manner to that described in the above Process 1-9. As the solvent used in the condensation, dichloromethane and the like can be illustrated. The reaction temperature is usually from 0° C. to room temperature, and the reaction time is usually from 1 hour to 1 day, varying based on a used starting material, solvent and reaction temperature.

The compounds represented by the above general formula (IV) used as starting materials in the above production process can be prepared in or according to a manner described in literature or an analogous method thereof. For example, a compound wherein $R^{23}$ represents a group of the general formula: —$OCH_2R^{33}$ in which $R^{33}$ has the same meaning as defined above, can be prepared according to the following procedures:

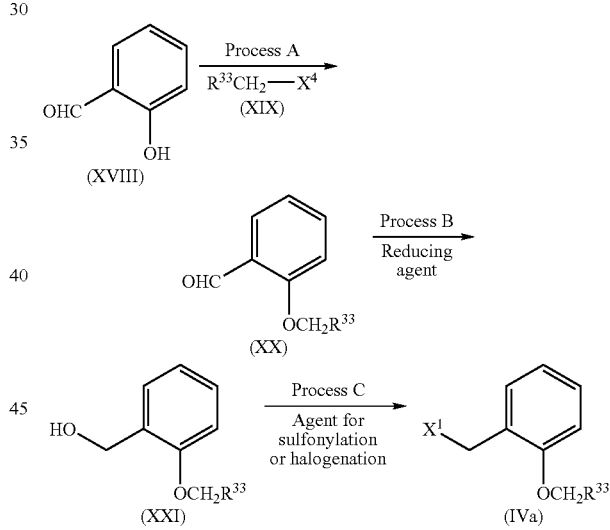

wherein $X^4$ represents a leaving group such as a halogen atom, a mesyloxy group, a tosyloxy group or the like; and $R^{33}$ and $X^1$ have the same meanings as defined above.

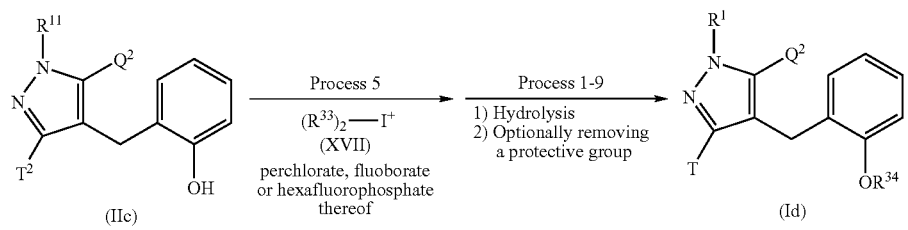

Process A

A compound represented by the above general formula (XX) can be prepared by subjecting a salicyl aldehyde represented by the above general formula (XVIII) to O-alkylation with a benzyl compound represented by the above general formula (XIX) in an inert solvent in the presence of a base such as potassium carbonate, cesium carbonate or the like. As the inert solvent used in the reaction, acetonitrile, ethanol, methanol, 1,2-dimethoxyethane, tetrahydrofuran, N,N-dimethylformamide, a mixed solvent thereof and the like can be illustrated. The reaction temperature is usually from 0° C. to reflux temperature, and the reaction time is usually from 1 hour to 1 day, varying based on a used starting material, solvent and reaction temperature.

Process B

A benzyl alcohol compound represented by the above general formula (XXI) can be prepared by reducing a compound represented by the above general formula (XX) in a various solvent using a reducing agent such as sodium borohydride, lithium aluminum hydride or the like. As the solvent used in the reaction, in case of using sodium borohydride as a reducing agent, a protic solvent such as methanol, ethanol or the like or a mixed solvent thereof with tetrahydrofuran, 1,2-dimethoxyethane and the like can be illustrated. In case of using lithium aluminum hydride or the like as a reducing agent, tetrahydrofuran, diethyl ether, 1,2-dimethoxyethane, a mixed solvent thereof and the like can be illustrated. The reaction temperature is usually from 0° C. to reflux temperature, and the reaction time is usually from 1 hour to 1 day, varying based on a used starting material, solvent and reaction temperature.

Process C

A benzyl compound represented by the above general formula (IVa) can be prepared by subjecting a compound represented by the above general formula (XXI) to: 1) sulfonylation using mesyl chloride or tosyl chloride in an inert solvent in the presence of a base such as triethylamine, diisopropylethylamine, pyridine or the like, or 2) halogenation using triphenylphosphine and either carbon tetrachloride or carbon tetrabromide in an inert solvent or without any solvent. As the solvent used in the sulfonylation, for example, acetonitrile, 1,2-dimethoxyethane, tetrahydrofuran, N,N-dimethylformamide, dichloromethane, a mixed solvent thereof and the like can be illustrated. The reaction temperature is usually from 0° C. to reflux temperature, and the reaction time is usually from 15 minutes to 12 hours, varying based on a used starting material, solvent and reaction temperature. As the solvent used in the halogenation, for example, dichloromethane, chloroform, a mixed solvent thereof and the like can be illustrated. The reaction temperature is usually from room temperature to ref lux temperature, and the reaction time is usually from 30 minutes to 1 day, varying based on a used starting material, solvent and reaction temperature.

The compounds represented by the above general formula (I) of the present invention obtained by the above production processes can be isolated and purified by conventional separation means such as fractional recrystallization, purification using chromatography, solvent extraction and solid phase extraction.

The glucopyranosyloxypyrazole derivatives represented by the above general formula (I) of the present invention can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like, salts with inorganic bases such as a sodium salt, a potassium salt and the like, and salts with organic bases such as arginine, lysine and the like.

The compounds represented by the above general formula (I) of the present invention include their solvates with pharmaceutically acceptable solvents such as water, ethanol or the like.

Among the glucopyranosyloxypyrazole derivatives represented by the above general formula (I) of the present invention and prodrugs thereof, there are two geometrical isomers in each compound having an unsaturated bond. In the present invention, either of cis(Z)-isomer or trans(E)-isomer can be employed.

Among the glucopyranosyloxypyrazole derivatives represented by the above general formula (I) of the present invention and prodrugs thereof, there are two optical isomers, R-isomer and S-isomer, in each compound having an asymmetric carbon atom excluding the glucopyranosyloxy moiety. In the present invention, either of R-isomer or S-isomer can be employed, and a mixture of both isomers can be also employed.

A prodrug of a compound represented by the above general formula (I) of the present invention can be prepared by introducing an appropriate group forming a prodrug into any one or more groups selected from a hydroxy group in a glucopyranosyl moiety or optionally at $R^1$ or $R^2$, a cyclic imino group in case that $R^1$ is a hydrogen atom, and an amino group in case that $R^3$ is an amino-substituted aryl group of a compound represented by the above general formula (I) in the usual way using a corresponding reagent to produce a prodrug such as a halide compound or the like, and then by optionally isolating and purifying the resulting compound in the usual way as occasion demands. As a group forming a prodrug used in a hydroxy group, a cyclic imino group or an amino group, for example, $C_{2-7}$ acyl group, a $C_{1-6}$ alkoxy-substituted ($C_{2-7}$ acyl) group, a $C_{2-7}$ alkoxycarbonyl-substituted ($C_{2-7}$ acyl) group, a $C_{2-7}$ alkoxycarbonyl group, a $C_{1-6}$ alkoxy($C_{2-7}$ alkoxycarbonyl group, a ($C_{2-7}$ acyloxy)methyl group, a 1-($C_{2-7}$ acyloxy)ethyl group, a ($C_{2-7}$ alkoxycarbonyl)oxymethyl group, a 1-[($C_{2-7}$ alkoxycarbonyl)oxy]ethyl group, a ($C_{3-7}$ cycloalkyl)oxycarbonyloxymethyl group, a 1-[($C_{3-7}$ cycloalkyl)oxycarbonyloxy]ethyl group and the like can be illustrated. The term "$C_{2-7}$ acyl group" means a straight-chained or branched acyl group having 2 to 7 carbon atoms such as an acetyl group, a propionyl group, a butyryl group, an isobutyryl group, a valeryl group, a pivaloyl group, a hexanoyl group or the like; and the term "$C_{1-6}$ alkoxy-substituted ($C_{2-7}$ acyl) group" means the above $C_{2-7}$ acyl group substituted by the above $C_{1-6}$ alkoxy group. The term "$C_{2-7}$ alkoxycarbonyl-substituted ($C_{2-7}$ acyl) group" means the above $C_{2-7}$ acyl group substituted by the above $C_{2-7}$ alkoxycarbonyl group; the term "$C_{1-6}$ alkoxy-substituted ($C_{2-7}$ alkoxycarbonyl) group" means the above $C_{2-7}$ alkoxycarbonyl group substituted by the above $C_{1-6}$ alkoxy group; and the term "($C_{2-7}$ acyloxy)methyl group" means a hydroxymethyl group O-substituted by the above $C_{2-7}$ acyl group. The term "1-($C_{2-7}$ acyloxy)ethyl group" means a 1-hydroxyethyl group O-substituted by the above $C_{2-7}$ acyl group; the term "($C_{2-7}$ alkoxycarbonyl)oxymethyl group" means a hydroxymethyl group O-substituted by the above $C_{2-7}$ alkoxycarbonyl group; and the term "1-[($C_{2-7}$ alkoxycarbonyl)oxy]ethyl group" means a 1-hydroxyethyl group O-substituted by the above $C_{2-7}$ alkoxycarbonyl group. The term "($C_{3-7}$ cycloalkyl)oxycarbonyl group" means a cyclic alkoxycarbonyl group containing the above $C_{3-7}$ cycloalkyl group; the term "($C_{3-7}$ cycloalkyl)oxycarbonyloxymethyl group" means a hydroxymethyl group O-substituted by the above ($C_{3-7}$ cycloalkyl)oxycarbonyl group; and the term "1-[($C_{3-7}$ cycloalkyl)oxycarbonyloxy]ethyl group" means a 1-hydroxyethyl group O-substituted by the above ($C_{3-7}$ cycloalkyl)oxycarbonyl group.

The glucopyranosyloxypyrazole derivatives represented by the above general formula (I) of the present invention, for example, showed a potent inhibitory activity in human SGLT1 in an assay for inhibitory effects on human SGLT1 activity as described below, and exerted an excellent inhibitory activity on blood glucose level increase in an assay for inhibitory effects on blood glucose level increase in rats. Thus, the glucopyranosyloxypyrazole derivatives represented by the above general formula (I) of the present invention show an excellent inhibitory activity in human SGLT1 in the small intestine and can markedly inhibit blood glucose level increase. Therefore, the glucopyranosyloxypyrazole derivatives represented by the above general formula of the present invention and prodrugs thereof are extremely useful as agents for the prevention or treatment of a disease associated with hyperglycemia, which is mediated by SGLT1 activity in the small intestine, such as diabetes, diabetic complications (e.g., retinopathy, neuropathy, nephropathy, ulcer, macroangiopathy), obesity, hyperinsulinemia, glucose metabolism disorder, hyperlipidemia, hypercholesterolemia, hypertriglyceridemia, lipid metabolism disorder, atherosclerosis, hypertension, congestive heart failure, edema, hyperuricemia, gout or the like.

Furthermore, the compounds of the present invention can be suitably used in combination with at least one member selected from drugs other than SGLT1 inhibitors. Examples of the drugs which can be used in combination with the compounds of the present invention include an insulin sensitivity enhancer, a glucose absorption inhibitor, a biguanide, an insulin secretion enhancer, a SGLT2 inhibitor, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhidantoin, EGB-761, bimoclomol, sulodexide, Y-128, a hydroxymethylglutaryl coenzyme A reductase inhibitor, a fibric acid derivative, a β3-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyltransferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blockade, a centrally acting antihypertensive agent, an $\alpha_2$-adrenoceptor agonist, an antiplatelets agent, a uric acid synthesis inhibitor, a uricosuric agent and a urinary alkalinizer.

In case of uses of the compound of the present invention in combination with the above one or more drugs, the present invention includes either dosage forms of simultaneous administration as a single preparation or separated preparations in way of the same or different administration route, and administration at different dosage intervals as separated preparations in way of the same or different administration route. A pharmaceutical combination comprising the compound of the present invention and the above one or more drugs includes both dosage forms as a single preparation and separated preparations for combination as mentioned above.

The compounds of the present invention can obtain more advantageous effects than additive effects in the prevention or treatment of the above diseases when using suitably in combination with the above one or more drugs. Also, the administration dose can be decreased in comparison with administration of either drug alone, or adverse effects of coadministrated drugs other than SGLT1 inhibitors can be avoided or declined.

Concrete compounds as the above drugs used for combination and preferable diseases to be treated are exemplified as follows. However, the present invention is not limited thereto, and for example, the concrete compounds include their free compounds, and their or other pharmaceutically acceptable salts.

As insulin sensitivity enhancers, peroxisome proliferator-activated receptor-γ agonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-α agonists such as GW-9578 and BM-170744, peroxisome proliferator-activated receptor-α/γ agonists such as GW-409544, KRP-297, NN-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-HO49020 and GW-501516 are illustrated. Insulin sensitivity enhancers are used preferably for diabetes, diabetic complications, obesity, hyperinsulinemia, glucose metabolism disorder, hyperlipidemia, hypercholesterolemia, atherosclerosis, and more preferably for diabetes, hyperinsulinemia or glucose metabolism disorder because of improving the disturbance of insulin signal transduction in peripheral tissues and enhancing glucose uptake into the tissues from the blood, leading to lowering blood glucose level.

As glucose absorption inhibitors, compounds as SGLT1 inhibitors are excluded, and α-glucosidase inhibitors such as acarbose, voglibose, miglitol, CKD-711, emiglitate, MDL-25,637, camiglibose and MDL-73,945, and α-amylase inhibitors such as AZM-127 are illustrated. Glucose absorption inhibitors are used preferably for diabetes, diabetic complications, obesity, hyperinsulinemia or glucose metabolism disorder, and more preferably for glucose metabolism disorder because of inhibiting the gastrointestinal enzymatic digestion of carbohydrates contained in foods, and inhibiting or delaying the absorption of glucose into the body.

As biguanides, phenformin, buformin hydrochloride, metformin hydrochloride and the like are illustrated. Biguanides are used preferably for diabetes, diabetic complications, hyperinsulinemia or glucose metabolism disorder, and more preferably for diabetes, hyperinsulinemia or glucose metabolism disorder because of lowering blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide and the like are illustrated. Insulin secretion enhancers are used preferably for diabetes, diabetic complications or glucose metabolism disorder, and more preferably for diabetes or glucose metabolism disorder because of lowering blood glucose level by acting on pancreatic β-cells and enhancing the insulin secretion.

As SGLT2 inhibitors, compounds including T-1095 described in official gazettes of Tokkai H10-237089, Tokkai 2001-288178, WO01/16147, WO01/27128, WO01/68660, WO01/74834, WO01/74835, WO02/28872 and the like can be illustrated. SGLT2 inhibitors are used preferably for diabetes, diabetic complications, obesity, hyperinsulinemia or glucose metabolism disorder, and more preferably for diabetes, obesity, hyperinsulinemia or glucose metabolism disorder because of lowering blood glucose level by inhibiting glucose absorption at the renal tubular.

As insulin or insulin analogues, human insulin, animal-derived insulin, human/animal-derived insulin analogues and the like are illustrated. These drugs are used preferably for diabetes, diabetic complications or glucose metabolism disorder, and more preferably for diabetes or glucose metabolism disorder.

As glucagon receptor antagonists, BAY-27-9955, NNC-92-1687 and the like are illustrated; as insulin receptor kinase stimulants, TER-17411, L-783281, KRX-613 and the like are illustrated; as tripeptidyl peptidase II inhibitors, UCL-1397 and the like are illustrated; as dipeptidyl peptidase IV inhibitors, NVP-DPP728A, TSL-225, P-32/98 and the like are illustrated; as protein tyrosine phosphatase 1B inhibitors, PTP-112, OC-86839, PNU-177496 and the like are illustrated; as glycogen phosphorylase inhibitors, NN-4201, CP-368296 and the like are illustrated; as fructose-bisphosphatase inhibitors, R-132917 and the like are illustrated; as pyruvate dehydrogenase inhibitors, AZD-7545 and the like are illustrated; as hepatic gluconeogenesis inhibitors, FR-225659 and the like are illustrated; as glucagon-like peptide-1 analogues, exendin-4, CJC-1131 and the like are illustrated; as glucagon-like peptide 1 agonists, AZM-134, LY-315902 and the like are illustrated; and as amylin, amylin analogues or amylin agonists, pramlintide acetate and the like are illustrated. These drugs, glucose-6-phosphatase inhibitors, D-chiroinositol, glycogen synthase kinase-3 inhibitors, glucagon-like peptide-1 are used preferably for diabetes, diabetic complications, hyperinsulinemia or glucose metabolism disorder, and more preferably for diabetes or glucose metabolism disorder.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat and the like are illustrated. Aldose reductase inhibitors are preferably used for diabetic complications because of inhibiting aldose reductase and lowering excessive intracellular accumulation of sorbitol in accelerated polyol pathway which are in continuous hyperglycemic condition in the tissues in diabetic complications.

As advanced glycation endproducts formation inhibitors, pyridoxamine, OPB-9195, ALT-946, ALT-711, pimagedine hydrochloride and the like are illustrated. Advanced glycation endproducts formation inhibitors are preferably used for diabetic complications because of inhibiting formation of advanced glycation endproducts which are accelerated in continuous hyperglycemic condition in diabetes and declining cellular damage.

As protein kinase C inhibitors, LY-333531, midostaurin and the like are illustrated. Protein kinase C inhibitors are preferably used for diabetic complications because of inhibiting protein kinase C activity which is accelerated in continuous hyperglycemic condition in diabetes.

As γ-aminobutyric acid receptor antagonists, topiramate and the like are illustrated; as sodium channel antagonists, mexiletine hydrochloride, oxcarbazepine and the like are illustrated; as transcrit factor NF-κB inhibitors, dexlipotam and the like are illustrated; as lipid peroxidase inhibitors, tirilazad mesylate and the like are illustrated; as N-acetylated-α-linked-acid-dipeptidase inhibitors, GPI-5693 and the like are illustrated; and as carnitine derivatives, carnitine, levacecamine hydrochloride, levocarnitine chloride, levocarnitine, ST-261 and the like are illustrated. These drugs, insulin-like growth factor-I, platelet-derived growth factor, platelet derived growth factor analogues, epidermal growth factor, nerve growth factor, uridine, 5-hydroxy-1-methylhidantoin, EGB-761, bimoclomol, sulodexide and Y-128 are preferably used for diabetic complications.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BA y-x-2678, BA y-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin and the like are illustrated. Hydroxymethylglutaryl coenzyme A reductase inhibitors are used preferably for hyperlipidemia, hypercholesterolemia, hypertriglyceridemia, lipid metabolism disorder or atherosclerosis, and more preferably for hyperlipidemia, hypercholesterolemia or atherosclerosis because of lowering blood cholesterol level by inhibiting hydroxymethylglutaryl coenzyme A reductase.

As fibric acid derivatives, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 and the like are illustrated. Fibric acid derivatives are used preferably for hyperinsulinemia, hyperlipidemia, hypercholesterolemia, hypertriglyceridemia, lipid metabolism disorder or atherosclerosis, and more preferably for hyperlipidemia, hypertriglyceridemia or atherosclerosis because of activating hepatic lipoprotein lipase and enhancing fatty acid oxidation, leading to lowering blood triglyceride level.

As $\beta_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 and the like are illustrated. $\beta_3$-Adrenoceptor agonists are used preferably for obesity, hyperinsulinemia, hyperlipidemia, hypercholesterolemia, hypertriglyceridemia or lipid metabolism disorder, and more preferably for obesity or hyperinsulinemia because of stimulating $\beta_3$-adrenoceptor in adipose tissue and enhancing the fatty acid oxidation, leading to induction of energy expenditure.

As acyl-coenzyme A: cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe and the like are illustrated. Acyl-coenzyme A: cholesterol acyltransferase inhibitors are used preferably for hyperlipidemia, hypercholesterolemia, hypertriglyceridemia or lipid metabolism disorder, and more preferably for hyperlipidemia or hypercholesterolemia because of lowering blood cholesterol level by inhibiting acyl-coenzyme A: cholesterol acyltransferase.

As thyroid hormone receptor agonists, sodium liothyronine, sodium levothyroxine, KB-2611 and the like are illustrated; as cholesterol absorption inhibitors, ezetimibe, SCH-48461 and the like are illustrated; as lipase inhibitors, orlistat, ATL-962, AZM-131, RED-103004 and the like are illustrated; as carnitine palmitoyltransferase inhibitors, etomoxir and the like are illustrated; as squalene synthase inhibitors, SDZ-268-198, BMS-188494, A-87049, RPR-101821, ZD-9720, RPR-107393, ER-27856 and the like are illustrated; as nicotinic acid derivatives, nicotinic acid, nicotinamide, nicomol, niceritrol, acipimox, nicorandil and the like are illustrated; as bile acid sequestrants, colestyramine, colestilan, colesevelam hydrochloride, GT-102-279 and the like are illustrated; as sodium/bile acid cotransporter inhibitors, 264W94, S-8921, SD-5613 and the like are illustrated; and as cholesterol ester transfer protein inhibitors, PNU-107368E, SC-795, JTT-705, CP-529414 and the like are illustrated. These drugs, probcol, microsomal triglyceride transfer protein inhibitors, lipoxygenase inhibitors and low-density lipoprotein receptor enhancers are preferably used for hyperlipidemia, hypercholesterolemia, hypertriglyceridemia or lipid metabolism disorder.

As appetite suppressants, monoamine uptake inhibitors, serotonin reuptake inhibitors, serotonin releasing stimulants, serotonin agonists (especially 5HT$_{2C}$-agonists), noradrenalin reuptake inhibitors, noradrenalin releasing stimulants, $\alpha_1$-adrenoceptor agonists, $\beta_2$-adrenoceptor agonists, dopamine agonists, cannabinoid receptor antagonists, $\gamma$-aminobutyric acid receptor antagonists, H$_3$-histamine antagonists, L-histidine, leptin, leptin analogues, leptin receptor agonists, melanocortin receptor agonists (especially, MC3-R agonists, MC4-R agonists), $\alpha$-melanocyte stimulating hormone, cocaine-and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotrophin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone antagonists, agouti-related protein inhibitors and orexin receptor antagonists are illustrated. Concretely, as monoamine uptake inhibitors, mazindol and the like are illustrated; as serotonin reuptake inhibitors, dexfenfluramine hydrochloride, fenfluramine, sibutramine hydrochloride, fluvoxamine maleate, sertraline hydrochloride and the like are illustrated; as serotonin agonists, inotriptan, (+)-norfenfluramine and the like are illustrated; as noradrenaline reuptake inhibitors, bupropion, GW-320659 and the like are illustrated; as noradrenaline releasing stimulants, rolipram, YM-992 and the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex and the like are illustrated; as dopamine agonists, ER-230, doprexin, bromocriptine mesylate and the like are illustrated; as cannabinoid receptor antagonists, rimonabant and the like are illustrated; as $\gamma$-aminobutyric acid receptor antagonists, topiramate and the like are illustrated; as H$_3$-histamine antagonists, GT-2394 and the like are illustrated; as leptin, leptin analogues or leptin receptor agonists, LY-355101 and the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 and the like are illustrated; and as neuropeptide Y antagonists, SR-120819-A, PD-160170, NGD-95-1, BIBP-3226, 1229-U-91, CGP-71683, BIBO-3304, CP-671906-01, J-115814 and the like are illustrated. Appetite suppressants are used preferably for diabetes, diabetic complications, obesity, glucose metabolism disorder, hyperlipidemia, hypercholesterolemia, hypertriglyceridemia, lipid metabolism disorder, atherosclerosis, hypertension, congestive heart failure, edema, hyperuricemia or gout, and more preferably for obesity because of stimulating or inhibiting the activities of intracerebral monoamines or bioactive peptides in central appetite regulatory system and suppressing the appetite, leading to reduction of energy intake.

As angiotensin-converting enzyme inhibitors, captopril, enalaprimaleate, alacepril, delaprilhydrochloride, ramipril, lisinopril, imidapril hydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril and the like are illustrated. Angiotensin-converting enzyme inhibitors are preferably used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril and the like are illustrated. Neutral endopeptidase inhibitors are preferably used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 and the like are illustrated. Angiotensin II receptor antagonists are preferably used for diabetic complications or hypertension.

As endothelin-converting enzyme inhibitors, CGS-31447, CGS-35066, SM-19712 and the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 and the like are illustrated. These drugs are preferably used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-α, PNU-80873A, isosorbide, D-mannitol, D-sorbitol, fructose, glycerin, acetazolamide, methazolamide, FR-179544, OPC-31260, lixivaptan, conivaptan hydrochloride and the like are illustrated. Diuretic drugs are preferably used for diabetic complications, hypertension, congestive heart failure or edema, and more preferably for hypertension, congestive heart failure or edema because of reducing blood pressure or improving edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride and the like are illustrated; as vasodilating antihypertensive agents, indapamide, todralazine hydrochloride, hydralazine hydrochloride, cadralazine, budralazine and the like are illustrated; as sympathetic blockades, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin and the like are illustrated; as centrally acting antihypertensive agents, reserpine and the like are illustrated; and as $\alpha_2$-adrenoceptor agonists, clonidine hydrochloride, methyldopa, CHF-1035, guanabenz acetate, guanfacine hydrochloride, moxonidine, lofexidine, ta lipexole hydrochloride and the like are illustrated. These drugs are preferably used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin and the like are illustrated. Antiplatelets agents are preferably used for atherosclerosis or congestive heart failure.

As uric acid synthesis inhibitors, allopurinol, oxypurinol and the like are illustrated; as uricosuric agents, benzbromarone, probenecid and the like are illustrated; and as urinary alkalinizers, sodium hydrogen carbonate, potassium citrate, sodium citrate and the like are illustrated. These drugs are preferably used for hyperuricemia or gout.

In case of uses in combination with drugs other than SGLT1 inhibitors, for example, in the use for diabetes, the combination with at least one member of the group consisting of an insulin sensitivity enhancer, a glucose absorption inhibitor, a biguanide, an insulin secretion enhancer, a SGLT2 inhibitor, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant is preferable; the combination with at least one member of the group consisting of an insulin sensitivity enhancer, a biguanide, an insulin secretion enhancer, a SGLT2 inhibitor, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue and an amylin agonist is more preferable; and the combination with at least one member of the group consisting of an insulin sensitivity enhancer, a biguanide, an insulin secretion enhancer, a SGLT2 inhibitor, and insulin or an insulin analogue is most preferable. Similarly, in the use for diabetic complications, the combination with at least one member of the group consisting of an insulin sensitivity enhancer, a glucose absorption inhibitor, a biguanide, an insulin secretion enhancer, a SGLT2 inhibitor, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhidantoin, EGB-761, bimoclomol, sulodexide, Y-128, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the combination with at least one member of the group consisting of an aldose reductase inhibitor, an angiotensin-converting enzyme inhibitor, a neutral endopeptidase inhibitor and an angiotensin II receptor antagonist is more preferable. Furthermore, in the use for obesity, the combination with at least one member of the group consisting of an insulin sensitivity enhancer, a glucose absorption inhibitor, a biguanide, an insulin secretion enhancer, a SGLT2 inhibitor, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant is preferable; and the combination with at least one member of the group consisting of a SGLT2 inhibitor, a $\beta_3$-adrenoceptor agonist and an appetite suppressant is more preferable.

When the pharmaceutical compositions of the present invention are employed in the practical treatment, various dosage forms are used depending on their uses. As examples of the dosage forms, powders, granules, fine granules, dry syrups, tablets, capsules, injections, solutions, ointments, suppositories, poultices and the like are illustrated, which are orally or parenterally administered.

These pharmaceutical compositions can be prepared by admixing with or by diluting and dissolving an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with pharmaceutically conventional methods depending on their dosage forms. In case of the use of the compound of the present invention in combination with the drugs other than SGLT1 inhibitors, they can be prepared by formulating each active ingredient together or individually.

When the pharmaceutical compositions of the present invention are employed in the practical treatment, the dosage of a compound represented by the above general formula (I), a pharmaceutically acceptable salt thereof or a prodrug thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably. Also, in case of the use of the compound of the present invention in combination with the drugs other than SGLT1 inhibitors, the dosage of the compound of the present invention can be decreased depending on the dosage of the drugs other than SGLT1 inhibitors.

The present invention is further illustrated in more detail by way of the following Reference Examples, Examples and Test Examples. However, the present invention is not limited thereto.

REFERENCE EXAMPLE 1

(2-Benzyloxyphenyl)methanol

2-Hydroxybenzaldehyde (19.3 g) and benzyl bromide (25.9 g) were dissolved in N,N-dimethylformamide (50 mL). Cesium carbonate (59.0 g) was added to the solution at 0° C., and the mixture was stirred at room temperature overnight. Water was added to the reaction mixture, and the mixture was extracted with diethyl ether. The organic layer was washed with 1 mol/L aqueous sodium hydroxide solution, water and brine successively, and dried over anhydrous magnesium sulfate. The solvent was removed under reduced pressure to give 2-benzyloxybenzaldehyde. This compound was dissolved in methanol (100 mL). Sodium borohydride (5.73 g) was added to the solution at 0° C., and the mixture was stirred at room temperature overnight. The reaction mixture was concentrated under reduced pressure, and water was added to the residue. The mixture was extracted with diethyl ether, and the organic layer was washed with 1 mol/L aqueous sodium hydroxide solution, water and brine successively, and dried over anhydrous magnesium sulfate. The solvent was removed under reduced pressure to give the title compound (32.4 g).

$^1$H-NMR (CDCl$_3$) δ ppm: 2.28 (1H, t, J=6.6 Hz), 4.74 (2H, d, J=6.6 Hz), 5.13 (2H, s), 6.93–7.00 (2H, m), 7.23–7.45 (7H, m)

REFERENCE EXAMPLE 2

[2-(2-Methylbenzyloxy)phenyl]methanol

The title compound was prepared in a similar manner to that described in Reference Example 1 using 2-methylbenzyl bromide instead of benzyl bromide.

$^1$H-NMR (CDCl$_3$) δ ppm: 2.24 (1H, t, J=6.6 Hz), 2.38 (3H, s), 4.71 (2H, d, J=6.6 Hz), 5.09 (2H, s), 6.94–7.02 (2H, m), 7.20–7.34 (5H, m), 7.37–7.42 (1H, m)

REFERENCE EXAMPLE 3

[2-(2,5-Dimethylbenzyloxy)phenyl]methanol

The title compound was prepared in a similar manner to that described in Reference Example 1 using 2,5-dimethylbenzyl mesylate instead of benzyl bromide.

$^1$H-NMR (CDCl$_3$) δ ppm: 2.26 (1H, t, J=6.6 Hz), 2.33 (6H, s), 4.71 (2H, d, J=6.6 Hz), 5.05 (2H, s), 6.94–7.20 (5H, m), 7.23–7.34 (2H, m)

REFERENCE EXAMPLE 4

[2-(Tetrahydropyran-4-yloxy)phenyl]methanol

The title compound was prepared in a similar manner to that described in Reference Example 1 using 4-tetrahydropyranyl mesylate instead of benzyl bromide.

$^1$H-NMR (CDCl$_3$) δ ppm: 1.78–1.86 (2H, m), 2.03–2.10 (2H, m), 2.27 (1H, t, J=6.5 Hz), 3.58–3.65 (2H, m), 3.94–4.01 (2H, m), 4.55–4.63 (1H, m), 4.72 (2H, d, J=6.5 Hz), 6.86–6.97 (2H, m), 7.23–7.33 (2H, m)

REFERENCE EXAMPLE 5

[2-(3-Methoxybenzyloxy)phenyl]methanol

The title compound was prepared in a similar manner to that described in Reference Example 1 using 3-methoxybenzyl mesylate instead of benzyl bromide.

¹H-NMR (CDCl₃) δ ppm: 2.29 (1H, t, J=6.6 Hz), 3.86 (3H, s), 4.75 (2H, d, J=6.6 Hz), 5.10 (2H, s), 6.84–6.88 (1H, m), 6.92–7.02 (4H, m), 7.23–7.32 (3H, m)

REFERENCE EXAMPLE 6

[2-(3-Methylbenzyloxy)phenyl]methanol

The title compound was prepared in a similar manner to that described in Reference Example 1 using 3-methylbenzyl mesylate instead of benzyl bromide.
¹H-NMR (CDCl₃) δ ppm: 2.32 (1H, t, J=6.6 Hz), 2.38 (3H, s), 4.74 (2H, d, J=6.6 Hz), 5.09 (2H, s), 6.93–6.99 (2H, m), 7.13–7.33 (6H, m)

REFERENCE EXAMPLE 7

(2-Phenoxyphenyl)methanol

2-Phenoxybenzoic acid (324 mg) was added gently to a suspension of lithium aluminum hydride (172 mg) in tetrahydrofuran (10 mL), and the mixture was stirred at room temperature overnight. Water (1 mL) was added gently to the reaction mixture, and the resulting mixture was stirred for 30 minutes. The reaction mixture was dried over anhydrous magnesium sulfate, and the solvent was removed under reduced pressure to give the title compound (256 mg).
¹H-NMR (CDCl₃) δ ppm: 2.00 (1H, t, J=6.4 Hz), 4.75 (2H, d, J=6.4 Hz), 6.85–6.89 (1H, m), 6.96–7.02 (2H, m), 7.07–7.16 (2H, m), 7.23–7.27 (1H, m), 7.31–7.36 (2H, m), 7.44–7.47 (1H, m)

REFERENCE EXAMPLE 8

(2-Phenoxymethylphenyl)methanol

The title compound was prepared in a similar manner to that described in Reference Example 7 using 2-phenoxymethylbenzoic acid instead of 2-phenoxybenzoic acid.
¹H-NMR (CDCl₃) δ ppm: 2.16 (1H, t, J=6.2 Hz), 4.76 (2H, d, J=6.2 Hz), 5.16 (2H, s), 6.97–7.03 (3H, m), 7.27–7.48 (6H, m)

REFERENCE EXAMPLE 9

[2-(4-Chlorobenzyloxy)phenyl]methanol

The title compound was prepared in a similar manner to that described in Reference Example 1 using 4-chlorobenzyl bromide instead of benzyl bromide.
¹H-NMR (CDCl₃) δ ppm: 2.17 (1H, t, J=6.5 Hz), 4.74 (2H, d, J=6.5 Hz), 5.09 (2H, s), 6.88–7.00 (2H, m), 7.23–7.38 (6H, m)

REFERENCE EXAMPLE 10

[2-(3-Chlorobenzyloxy)phenyl]methanol

The title compound was prepared in a similar manner to that described in Reference Example 1 using 3-chlorobenzyl bromide instead of benzyl bromide.
¹H-NMR (CDCl₃) δ ppm: 2.16 (1H, br-s), 4.76 (2H, br-s), 5.10 (2H, s), 6.88–6.93 (1H, m), 6.96–7.02 (1H, m), 7.23–7.37 (5H, m), 7.41–7.42 (1H, m)

REFERENCE EXAMPLE 11

[2-(2-Chlorobenzyloxy)phenyl]methanol

The title compound was prepared in a similar manner to that described in Reference Example 1 using 2-chlorobenzyl bromide instead of benzyl bromide.

¹H-NMR (CDCl₃) δ ppm: 2.25 (1H, t, J=6.2 Hz), 4.76 (2H, d, J=6.2 Hz), 5.22 (2H, s), 6.93–7.02 (2H, m), 7.26–7.35 (4H, m), 7.38–7.43 (1H, m), 7.50–7.53 (1H, m)

REFERENCE EXAMPLE 12

(2-Methoxymethoxyphenyl)methanol

The title compound was prepared in a similar manner to that described in Reference Example 1 using chloromethyl methyl ether instead of benzyl bromide.
¹H-NMR (CDCl₃) δ ppm: 2.27 (1H, t, J=6.5 Hz), 3.50 (3H, s), 4.71 (2H, d, J=6.5 Hz), 5.24 (2H, s), 6.99–7.03 (1H, m), 7.08–7.12 (1H, m), 7.23–7.33 (2H, m)

REFERENCE EXAMPLE 13 m-Tolyl Acetate

Acetic anhydride (519 mg) and pyridine (439 mg) were added to a solution of 3-methylphenol (500 mg) in dichloromethane (10 mL), and the mixture was stirred at room temperature for 12 hours. The reaction mixture was poured into 1 mol/L hydrochloric acid, and the resulting mixture was extracted with diethyl ether. The organic layer was washed with a saturated aqueous sodium hydrogen carbonate solution and water successively, and dried over anhydrous magnesium sulfate. The solvent was removed under reduced pressure, and the residue was purified by column chromatography on silica gel (eluent: ethyl acetate/hexane=1/8) to give the title compound (583 mg).
¹H-NMR (CDCl₃) δ ppm: 2.29 (3H, s), 2.35 (3H, s), 6.85–6.95 (2H, m), 7.00–7.10 (1H, m), 7.20–7.30 (1H, m)

REFERENCE EXAMPLE 14

3-Bromomethylphenyl acetate

A suspension of m-tolyl acetate (583 mg), N-bromosuccinimide (691 mg) and α,α'-azobis(isobutyronitrile) (13 mg) in tetrachloromethane (10 mL) was refluxed for 1 hour. The reaction mixture was cooled to room temperature, and the insoluble material was removed by filtration. The filtrate was concentrated to give the title compound (893 mg).
¹H-NMR (CDCl₃) δ ppm: 2.30 (3H, s), 4.47 (2H, s), 7.00–7.10 (1H, m), 7.10–7.20 (1H, m), 7.20–7.40 (2H, m)

REFERENCE EXAMPLE 15

O-Benzyl 4-methyl-3-oxothiopentanoate

A solution of S-methyl O-benzyl dithiocarbonate (6.90 g) and 3-methylbutan-2-one (3.00 g) in toluene (20 mL) was added dropwise to a suspension of sodium amide (2.71 g) in toluene (60 mL) at 0° C. over a 5-minute period. The mixture was stirred at room temperature for 2 hours. The reaction mixture was poured into water, and the mixture was acidified by addition of 1 mol/L hydrochloric acid. The resulting mixture was extracted with diethyl ether, and the organic layer was washed with water and dried over anhydrous magnesium sulfate. The solvent was removed under reduced pressure, and the residue was purified by column chromatography on silica gel (eluent: hexane/ethyl acetate=10/1) to give the title compound (5.90 g).
¹H-NMR (CDCl₃) δ ppm: 1.17 (6H, d, J=6.9 Hz), 2.45 (1H, heptet, J=6.9 Hz), 5.45 (2H, s), 5.77 (1H, s), 7.30–7.45 (5H, m), 13.77 (1H, s)

REFERENCE EXAMPLE 16

3-Benzyloxy-1-(2-hydroxyethyl)-5-isopropyl-1H-pyrazole

2-Hydroxyethylhydrazine (1.90 g) was added to a solution of O-Benzyl 4-methyl-3-oxothiopentanoate (5.90 g) and triethylamine (5.05 g) in acetonitrile (60 mL), and the mixture was stirred at room temperature for 3 hours. The reaction mixture was poured into water, and the mixture was extracted with diethyl ether. The organic layer was washed with brine and dried over anhydrous magnesium sulfate. The solvent was removed under reduced pressure, and the residue was purified by column chromatography on silica gel (eluent: hexane/ethyl acetate=1/1) to give the title compound (5.90 g).
$^1$H-NMR (CDCl$_3$) δ ppm: 1.22 (6H, d, J=6.8 Hz), 2.86 (1H, heptet, J=6.8 Hz), 3.78 (1H, t, J=6.0 Hz), 3.90–4.05 (4H, m), 5.14 (2H, s), 5.50 (1H, s), 7.25–7.50 (5H, m)

REFERENCE EXAMPLE 17

1-(2-Benzoyloxyethyl)-3-benzyloxy-5-isopropyl-1H-pyrazole

To a solution of 3-benzyloxy-1-(2-hydroxyethyl)-5-isopropyl-1H-pyrazole (2.41 g) in dichloromethane (45 mL) were added triethylamine (1.40 g) and benzoyl chloride (1.43 g) at 0° C., and the mixture was stirred for 30 minutes. The reaction mixture was poured into water, and the mixture was extracted with ethyl acetate. The organic layer was washed with water and dried over anhydrous magnesium sulfate. The solvent was removed under reduced pressure, and the residue was purified by column chromatography on silica gel (eluent: ethyl acetate/hexane=1/6-1/1) to give the title compound (1.35 g).
$^1$H-NMR (CDCl$_3$) δ ppm: 1.20 (6H, d, J=6.8 Hz), 2.92 (1H, heptet, J=6.8 Hz), 4.28 (2H, t, J=5.7 Hz), 4.67 (2H, t, J=5.7 Hz), 5.15 (2H, s), 5.49 (1H, s), 7.20–7.60 (8H, m), 7.90–8.05 (2H, m)

REFERENCE EXAMPLE 18

1-(2-Benzoyloxyethyl)-3-benzyloxy-4-formyl-5-isopropyl-1H-pyazole

To a solution of 1-(2-benzoyloxyethyl)-3-benzyloxy-5-isopropyl-1H-pyrazole (1.35 g) in N,N-dimethylformamide (8 mL) was added phosphorus oxychloride (625 mg) at 80° C., and the mixture was stirred for 1 hour. After the reaction mixture was cooled to room temperature and poured into a saturated aqueous sodium hydrogen carbonate solution, the resulting mixture was extracted with diethyl ether. The organic layer was washed with water and dried over anhydrous magnesium sulfate. The solvent was removed under reduced pressure, and the residue was purified by column chromatography on silica gel (eluent: ethyl acetate/hexane=1/3) to give the title compound (1.20 g).
$^1$H-NMR (CDCl$_3$) δ ppm: 1.34 (6H, d, J=7.1 Hz), 3.28 (1H, heptet, J=7.1 Hz), 4.38 (2H, t, J=5.5 Hz), 4.70 (2H, t, J=5.5 Hz), 5.26 (2H, s), 7.25–7.65 (8H, m), 7.95–8.05 (2H,m), 9.84 (1H, s)

REFERENCE EXAMPLE 19

4-(2-Benzyloxybenzyl)-1-(2-benzyloxyethyl)-3-(β-D-glucopyranosyloxy)-5-trifluoromethyl-1H-pyrazole To a solution of 4-(2-benzyloxybenzyl)-3-(β-D-glucopyranosyloxy)-5-trifluoromethyl-1H-pyrazole (300 mg) in N,N-dimethylformamide (3 mL) were added (2-bromoethoxymethyl)benzene (379 mg) and cesium carbonate (957 mg), and the mixture was stirred at 80° C. for 1.5 hours. The reaction mixture was poured into water, and the mixture was extracted with ethyl acetate. The organic layer was washed with water and dried over anhydrous magnesium sulfate. The solvent was removed under reduced pressure, and the residue was purified by column chromatography on silica gel (eluent: dichloromethane/methanol=20/1-10/1) to give the title compound (154 mg).
$^1$H-NMR (CD$_3$OD) δ ppm: 3.25–3.40 (4H, m), 3.63 (1H, dd, J=5.0, 12.0 Hz), 3.76 (1H, dd, J=2.3, 12.0 Hz), 3.80–3.90 (2H, m), 3.91 (2H, s), 4.31 (2H, t, J=5.4 Hz), 4.48 (2H, s), 5.13 (2H, s), 5.28 (1H, d, J=7.4 Hz), 6.70–6.80 (1H, m), 6.86 (1H, d, J=7.3 Hz), 6.90–7.00 (1H, m), 7.05–7.15 (1H, m), 7.20–7.45 (10H, m)

REFERENCE EXAMPLE 20

(2-Cycloheptyloxyphenyl)methanol

The title compound was prepared in a similar manner to that described in Reference Example 1 using cycloheptylmesylate instead of benzyl bromide.
$^1$H-NMR (CDCl$_3$) δ ppm: 1.35–1.90 (10H, m), 2.00–2.10 (2H, m), 2.52 (1H, t, J=6.5 Hz), 4.45–4.55 (1H, m), 4.67 (2H, d, J=6.5 Hz), 6.80–6.95 (2H, m), 7.20–7.30 (2H, m)

REFERENCE EXAMPLE 21

4-(2-Benzyloxybenzyl)-1-(2-benzyloxyethyl)-5-ethyl-3-(β-D-glucopyranosyloxy)-1H-pyrazole The title compound was prepared in a similar manner to that described in Reference Example 19 using 4-(2-benzyloxybenzyl)-5-ethyl-3-(β-D-glucopyranosyloxy)-1H-pyrazole instead of 4-(2-benzyloxybenzyl)-3-(β-D-glucopyranosyloxy)-5-trifluoromethyl-1H-pyrazole.
$^1$H-NMR (CD$_3$OD) δ ppm: 0.86 (3H, t, J=7.7 Hz), 2.47 (2H, q, J=7.7 Hz), 3.20–3.45 (4H, m), 3.64 (1H, dd, J=5.3, 12.0 Hz), 3.70–3.85 (5H, m), 4.05–4.15 (2H, m), 4.35–4.45 (2H, m), 5.00–5.15 (3H, m), 6.75–6.85 (1H, m), 6.96 (1H, d, J=7.7 Hz), 7.05–7.50 (12H, m)

REFERENCE EXAMPLE 22

(3-tert-Butyldimethylsilyloxymethylphenyl)methanol

To a solution of 1,3-benzenedimethanol (1 g) in tetrahydrofuran (10 mL) was added sodium hydride (60%, 318 mg) under ice-cooling, and the mixture was stirred for 30 minutes. To the reaction mixture was added tert-butyldimethylsilyl chloride (1.09 g), and the mixture was stirred at room temperature for 4 days. Ice water was added to the reaction mixture, and the resulting mixture was extracted with diethyl ether. The extract was washed with water and dried over anhydrous magnesium sulfate. The solvent was removed under reduced pressure, and the residue was purified by column chromatography on silica gel (eluent: hexane/ethyl acetate=5/1) to give the title compound (528 mg).
$^1$H-NMR (CDCl$_3$) δ ppm: 0.10 (6H, s), 0.95 (9H, s), 1.59 (1H, t, J=5.9 Hz), 4.70 (2H, d, J=5.9 Hz), 4.75 (2H, s), 7.20–7.40 (4H, m)

REFERENCE EXAMPLE 23

3-tert-Butyldimethylsilyloxymethylbenzyl bromide

To a solution of (3-tert-butyldimethylsilyloxymethylphenyl)methanol (528 mg) and tetrabromomethane (694 mg) in dichloromethane (10 mL) was added triphenylphosphine (549 mg) at room temperature, and the mixture was stirred for 2 hours. The reaction mixture was purified by column chromatography on silica gel (eluent: hexane/ethyl acetate=5/1) to give the title compound (660 mg).

$^1$H-NMR (CDCl$_3$) δ ppm: 0.10 (6H, s), 0.95 (9H, s), 4.50 (2H, s), 4.73 (2H, s), 7.20–7.40 (4H, m)

EXAMPLE 1

4-(2-Benzyloxybenzyl)-5-tert-butyl-1,2-dihydropyrazol-3-one

To a solution of (2-benzyloxyphenyl)methanol (214 mg) and triethylamine (140 μL) in tetrahydrofuran (1 mL) was added methanesulfonyl chloride (115 μL) at 0° C., and the mixture was stirred at room temperature for 1 hour. The insoluble material was removed by filtration. The obtained solution of (2-benzyloxyphenyl)methyl mesylate in tetrahydrofuran was added to a suspension of sodium hydride (60%, 40 mg) and methyl 4,4-dimethyl-3-oxopentanoate in 1,2-dimethoxyethane (2 mL), and the mixture was stirred at 80° C. overnight. To the reaction mixture was added 0.5 mol/L Hydrochloric acid, and the resulting mixture was extracted with diethyl ether. The organic layer was dried over anhydrous magnesium sulfate, and the solvent was removed under reduced pressure. To a solution of the residue in toluene (2 mL) was added hydrazine monohydrate (0.146 mL), and the mixture was stirred at 110° C. overnight. Water was added to the reaction mixture, and the resulting mixture was extracted with ethyl acetate. The organic layer was dried over anhydrous magnesium sulfate, and the solvent was removed under reduced pressure. The residue was purified by column chromatography on aminopropyl silica gel (eluent: hexane/ethyl acetate=1/1-methanol) to give the title compound (20 mg).

$^1$H-NMR (CDCl$_3$) δ ppm: 1.24 (9H, s), 3.92 (2H, s), 5.14 (2H, s), 6.83–6.93 (2H, m), 6.99–7.03 (1H, m), 7.12–7.17 (1H, m), 7.32–7.35 (1H, m), 7.37–7.42 (2H, m), 7.46–7.49 (2H, m)

EXAMPLE 2

4-(2-Benzyloxybenzyl)-3-(β-D-glucopyranosyloxy)-5-isopropyl-1H-pyrazole

To a suspension of 4-(2-benzyloxybenzyl)-5-isopropyl-1, 2-dihydropyrazol-3-one (114 mg) and acetobromo-α-D-glucose (173 mg) in acetonitrile (2 mL) was added silver carbonate (127 mg), and the mixture was stirred under shading the light at room temperature for 3 days. The reaction mixture was purified by column chromatography on aminopropyl silica gel (eluent: ethyl acetate/hexane=1/1) to give 5-isopropyl-4-(2-benzyloxybenzyl)-3-(2,3,4,6-tetra-O-acetyl-β-D-glucopyranosyloxy)-1H-pyrazole. To a solution of 5-isopropyl-4-(2-benzyloxybenzyl)-3-(2,3,4,6-tetra-O-acetyl-β-D-glucopyranosyloxy)-1H-pyrazole in tetrahydrofuran (1 mL) and methanol (0.5 mL) was added sodium methoxide (28% methanol solution, 50 μL), and the mixture was stirred at room temperature for 1 hour. The reaction mixture was concentrated under reduced pressure, and the residue was purified by column chromatography on silica gel (eluent: dichloromethane/methanol=10/1-5/1) to give the title compound (22 mg).

$^1$H-NMR (CD$_3$OD) δ ppm: 1.04–1.07 (6H, m), 2.81–2.90 (1H, m), 3.30–3.40 (4H, m), 3.62–3.67 (1H, m), 3.77–3.83 (3H, m), 5.04–5.08 (1H, m), 5.13 (2H, s), 6.77–6.84 (1H, m), 6.93–6.97 (1H, m), 7.03–7.13 (2H, m), 7.27–7.46 (5H, m)

EXAMPLE 3

4-(2-Benzyloxybenzyl)-3-(β-D-glucopyranosyloxy)-5-pentafluoroethyl-1H-pyrazole

To a solution of 4-(2-benzyloxybenzyl)-5-pentafluoroethyl-1,2-dihydropyrazol-3-one (55 mg) and acetobromo-α-D-glucose (63 mg) in acetonitrile (2 mL) was added potassium carbonate (23 mg), and the mixture was stirred at room temperature for 3 days. The reaction mixture was purified by column chromatography on aminopropyl silica gel (eluent: ethyl acetate/hexane=1/1-ethyl acetate) to give 4-(2-benzyloxybenzyl)-5-pentafluoroethyl-3-(2,3,4,6-tetra-O-acetyl-β-D-glucopyranosyloxy)-1H-pyrazole. To a solution of 4-(2-benzyloxybenzyl)-5-pentafluoroethyl-3-(2,3,4,6-tetra-O-acetyl-β-D-glucopyranosyloxy)-1H-pyrazole in tetrahydrofuran (1 mL) and methanol (0.5 mL) was added sodium methoxide (28% methanol solution, 50 μL), and the mixture was stirred at room temperature overnight. The reaction mixture was concentrated under reduced pressure, and the residue was purified by column chromatography on silica gel (eluent: dichloromethane/methanol=10/1-5/1) to give the title compound (33 mg).

$^1$H-NMR (CD$_3$OD) δ ppm: 3.30–3.40 (4H, m), 3.64–3.68 (1H, m), 3.78–3.83 (1H, m), 3.87–3.97 (2H,m), 5.13 (2H, s), 5.18–5.32 (1H, m), 6.77–6.88 (2H, m), 6.93–6.96 (1H, m), 7.08–7.12 (1H, m), 7.25–7.45 (5H, m)

EXAMPLE 4

3-(β-D-Glucopyranosyloxy)-5-isopropyl-4-[2-(2-methylbenzyloxy)benzyl]-1H-pyrazole To a solution of 5-isopropyl-4-[2-(2-methylbenzyloxy)-benzyl]-1,2-dihydropyrazol-3-one (68 mg), acetobromo-α-D-glucose (92 mg) and benzyl tri(n-butyl)ammonium chloride (63 mg) in dichloromethane (2 mL) was added a solution of potassium carbonate (140 mg) in water (0.5 mL), and the mixture was stirred at room temperature overnight. The reaction mixture was extracted with dichloromethane. The organic layer was dried over anhydrous magnesium sulfate, and the solvent was removed under reduced pressure to give a residue containing 5-isopropyl-4-[2-(2-methylbenzyloxy)benzyl]-3-(2,3,4,6-tetra-O-acetyl-β-D-glucopyranosyloxy)-1H-pyrazole. To a solution of the residue in tetrahydrofuran (1 mL) and methanol (0.5 mL) was added sodium methoxide (28% methanol solution, 0.187 mL), and the mixture was stirred at room temperature for 1 hour. The reaction mixture was neutralized with 2 mol/L hydrochloric acid and concentrated under reduced pressure, and the residue was purified by chromatography on silica gel (eluent: dichloromethane/methanol=10/1-5/1) to give the title compound (51 mg).

$^1$H-NMR (CD$_3$OD) δ ppm: 0.98–1.08 (6H, m), 2.38 (3H, s), 2.75–2.85 (1H, m), 3.48–3.42 (4H, m), 3.60–3.85 (4H, m), 5.03–5.08 (3H, m), 6.80–6.84 (1H, m), 6.96–7.24 (6H, m), 7.37–7.41 (1H, m)

EXAMPLE 5

4-[2-(2,5-Dimethylbenzyloxy)benzyl]-3-(β-D-glucopyranosyloxy)-5-isopropyl-1H-pyrazole To a solution of 4-[2-(2,5-dimethylbenzyloxy)benzyl]-5-isopropyl-1,2-dihydropyrazol-3-one (152 mg) in N,N-dimethylformamide (1 mL) was added sodium hydride (60%, 18 mg), and the mixture was stirred at room temperature for 15 minutes. To the reaction mixture was added a solution of acetobromo-α-D-glucose (214 mg) in N,N-dimethylformamide (1 mL), and the resulting mixture was stirred at room temperature overnight. Water was added to the reaction mixture, and the mixture was extracted with ethyl acetate. The organic layer was dried over anhydrous magnesium sulfate, and the solvent was removed under reduced pressure. The residue was purified by column chromatography on aminopropyl silica gel (eluent: ethyl acetate/hexane=1/1-ethyl acetate) to give 4-[2-(2,5-dimethylbenzyloxy)benzyl]-5-isopropyl-3-(2,3,4,6-tetra-O-acetyl-β-D-glucopyranosyloxy)-1H-pyrazole. To a solution of 4-[2-(2,5-dimethylbenzyloxy)benzyl]-5-isopropyl-3-(2,3,4,6-tetra-O-acetyl-β-D-glucopyranosyloxy)-1H-pyrazole in tetrahydrofuran (1 mL) and methanol (0.5 mL) was added sodium methoxide (28% methanol solution, 0.400 mL), and the mixture was stirred at room temperature overnight. The reaction mixture was neutralized with 2 mol/L hydrochloric acid and concentrated under reduced pressure, and the residue was purified by chromatography on silica gel (eluent: dichloromethane/methanol=10/1–5/1) to give the title compound (33 mg).

$^1$H-NMR (CD$_3$OD) δ ppm: 0.97–1.08 (6H, m), 2.33 (3H, s), 2.37 (3H, s), 2.76–2.90 (1H, m), 3.25–3.43 (4H, m), 3.63–3.87 (4H, m), 5.00–5.10 (3H, m), 6.76–6.88 (1H, m), 6.95–7.23 (6H, m)

EXAMPLE 6

3-(β-D-Glucopyranosyloxy)-4-(2-hydroxybenzyl)-5-isopropyl-1H-pyrazole

To a solution of 4-(2-benzyloxybenzyl)-3-(β-D-glucopyranosyloxy)-5-isopropyl-1H-pyrazole (200 mg) in methanol (5 mL) was added 10% palladium-carbon powder (40 mg), and the mixture was stirred at room temperature under a hydrogen atmosphere for 3 hours. The insoluble material was removed by filtration, and the fírtrate was concentrated under reduced pressure. The residue was purified by column chromatography on silica gel (eluent: dichloromethane/methanol=6/1) to give the title compound (146 mg).

$^1$H-NMR (CD$_3$OD) δ ppm: 1.09–1.22 (6H, m), 2.88–3.00 (1H, m), 3.29–3.45 (4H, m), 3.63–3.88 (4H,m), 5.05–5.12 (1H, m), 6.66–6.77 (2H, m), 6.90–6.98 (2H, m)

EXAMPLE 7

4-(2-Hydroxybenzyl)-1-(2-hydroxyethyl)-5-isopropyl-1,2-dihydropyrazol-3-one

To a solution of 2-benzyloxybromobenzene (1.66 g) in tetrahydrofuran (50 mL) was added tert-butyllithium (1.6 mol/L pentane solution, 4.33 mL) at −78° C. under an argon atmosphere, and the mixture was stirred for 5 minutes. To the reaction mixture was added a solution of 1-(2-benzoyloxyethyl)-3-benzyloxy-4-formyl-5-isopropyl-1H-pyrazole (620 mg) in tetrahydrofuran (5 mL), and the mixture was stirred at 0° C. for 30 minutes. To the reaction mixture was added a saturated aqueous ammonium chloride solution, and the resulting mixture was extracted with ethyl acetate. The organic layer was dried over anhydrous magnesium sulfate, and the solvent was removed under reduced pressure. The residue was purified by column chromatography on silica gel (eluent: ethyl acetate/hexane=1/1–2/1) to give 2-{3-benzyloxy-4-[(2-benzyloxyphenyl)hydroxymethyl]-5-isopropylpyrazol-1-yl}ethanol (448 mg). To a solution of 2-{3-benzyloxy-4-[(2-benzyloxyphenyl)hydroxymethyl]-5-isopropylpyrazol-1-yl}ethanol (448 mg) in methanol (5 mL) was added 10% palladium-carbon powder (448 mg), and the mixture was stirred at room temperature under a hydrogen atmosphere for 3 hours. The insoluble material was removed by filtration, and the solvent of the filtrate was removed under reduced pressure to give the title compound (220 mg).

$^1$H-NMR (CDCl$_3$) δ ppm: 1.35 (6H, d, J=7.2 Hz), 3.10–3.25 (1H, m), 3.64 (2H, s), 3.85–4.05 (4H, m), 6.75–6.90 (2H, m), 7.00–7.15 (2H, m)

EXAMPLE 8

4-(2-Hydroxybenzyl)-1-(2-hydroxyethyl)-5-isopropyl-3-(2,3,4,6-tetra-O-acetyl-β-D-glucopyranosyloxy)-1H-pyrazole To a solution of 4-(2-hydroxybenzyl)-1-(2-hydroxyethyl)-5-isopropyl-1,2-dihydropyrazol-3-one (90 mg), acetobromo-α-D-glucose (161 mg) and benzyl tri(n-butyl)ammonium chloride (101 mg) in dichloromethane (5 mL) was added 2 mol/L aqueous sodium hydroxide solution (0.81 mL), and the mixture was stirred at room temperature for 3 hours. The reaction mixture was purified by column chromatography on aminopropyl silica gel (eluent: ethyl acetate/hexane 1/1—ethyl acetate) to give the title compound (35 mg).

$^1$H-NMR (CDCl$_3$) δ ppm: 1.16 (3H, d, J=7.2 Hz), 1.19 (3H, d, J=7.2 Hz), 1.89 (3H, s), 2.01 (3H, s), 2.03 (3H, s), 2.08 (3H, s), 3.00–3.20 (1H, m), 3.60–3.75 (2H, m), 3.80–4.30 (7H, m), 5.10–5.30 (3H, m), 5.50 (1H, d, J=7.8 Hz), 5.60–5.80 (1H,br-s), 6.70–6.85 (2H, m), 6.90–7.00 (1H, m), 7.00–7.10 (1H, m)

EXAMPLE 9

4-(2-Benzyloxybenzyl)-3-(β-D-glucopyranosyloxy)-1-(2-hydroxyethyl)-5-isopropyl-1H-pyrazole To a solution of 4-(2-hydroxybenzyl)-1-(2-hydroxyethyl)-5-isopropyl-3-(2,3,4,6-tetra-O-acetyl-β-D-glucopyranosyloxy)-1H-pyrazole (35 mg) in N,N-dimethylformamide (3 mL) were added benzyl bromide (20 mg) and potassium carbonate (18 mg), and the mixture was stirred at room temperature for 14 hours. The reaction mixture was poured into water, and the resulting mixture was extracted with ethyl acetate. The organic layer was washed with water and dried over anhydrous magnesium sulfate. The solvent was removed under reduced pressure, and the residue was purified by column chromatography on silica gel (eluent: hexane/ethyl acetate=1/3—ethyl acetate) to give 4-(2-benzyloxybenzyl)-1-(2-hydroxyethyl)-5-isopropyl-3-(2,3,4,6-tetra-O-acetyl-β-D-glucopyranosyloxy)-1H-pyrazole (33 mg). To a solution of 4-(2-benzyloxybenzyl)-1-(2-hydroxyethyl)-5-isopropyl-3-(2,3,4,6-tetra-O-acetyl-β-D-glucopyranosyloxy)-1H-pyrazole (33 mg) in methanol (3 mL) was added sodium methoxide (28% methanol solution, 9 μL), and the mixture was stirred at room temperature for 1 hour. The reaction mixture was concentrated under reduced pressure, and the residue was purified by solid phase extraction on ODS (washing solvent: distilled water, eluent: methanol) to give the title compound (20 mg).

$^1$H-NMR (CD$_3$OD) δ ppm: 1.00–1.15 (6H, m), 3.00–3.20 (1H, m), 3.25–3.40 (4H, m), 3.65 (1H, dd, J=5.1, 12.0 Hz), 3.75–3.90 (5H, m), 4.07 (2H, t, J=5.9 Hz), 5.05–5.20 (3H, m), 6.75–6.85 (1H, m), 6.90–7.05 (2H, m), 7.05–7.15 (1H, m), 7.25–7.55 (5H, m)

EXAMPLE 10

3-(β-D-Glucopyranosyloxy)-4-(2-hydroxybenzyl)-1-(2-hydroxyethyl)-5-trifluoromethyl-1H-pyrazole The title compound was prepared in a similar manner to that described in Example 6 using 4-(2-benzyloxybenzyl)-1-(2-benzyloxyethyl)-3-(β-D-glucopyranosyloxy)-5-trifluoromethyl-1H-pyrazole instead of 4-(2-benzyloxybenzyl)-3-(β-glucopyranosyloxy)-5-isopropyl-1H-pyrazole.

$^1$H-NMR (CD$_3$OD) δ ppm: 3.25–3.45 (4H, m), 3.65 (1H, dd, J=5.0, 12.1 Hz), 3.75–3.95 (5H, m), 4.20 (2H, t, J=5.9 Hz), 5.29 (1H, d, J=7.6 Hz), 6.60–6.85 (3H, m), 6.90–7.05 (1H, m)

EXAMPLE 11

4-(2-Benzyloxybenzyl)-3-(β-D-glucopyranosyloxy)-1-(2-hydroxyethyl)-5-trifluoromethyl-1H-pyrazole To a solution of 3-(β-D-glucopyranosyloxy)-4-(2-hydroxybenzyl)-1-(2-hydroxyethyl)-5-trifluoromethyl-1H-pyrazole (111 mg) in N,N-dimethylformamide (0.5 mL) were added benzyl bromide (49 mg) and potassium carbonate (43 mg), and the mixture was stirred at room temperature for 15 hours. The reaction mixture was poured into water, and the resulting mixture was extracted with ethyl acetate. The organic layer was washed with water and dried over anhydrous magnesium sulfate, and the solvent was removed under reduced pressure. The residue was purified by column chromatography on silica gel (eluent: dichloromethane/methanol=10/1–5/1) to give the title compound (108 mg).

$^1$H-NMR (CD$_3$OD) δ ppm: 3.25–3.45 (4H, m), 3.64 (1H, dd, J=4.5, 12.1 Hz), 3.80 (1H, dd, J=1.7, 12.1 Hz), 3.85–4.00 (4H, m), 4.20 (2H, t, J=6.0 Hz), 5.14 (2H, s), 5.31 (1H, d, J=7.6 Hz), 6.75–7.00 (3H, m), 7.05–7.15 (1H, m), 7.25–7.50 (5H, m)

EXAMPLE 12

3-(β-D-Glucopyranosyloxy)-4-[2-(3-hydroxybenzyloxy)benzyl]-5-isopropyl-1H-pyrazole To a solution of 3-(β-D-glucopyranosyloxy)-4-(2-hydroxybenzyl)-5-isopropyl-1H-pyrazole (150 mg) in N,N-dimethylformamide (1 mL) were added 3-bromomethylphenyl acetate (131 mg) and potassium carbonate (105 mg), and the mixture was stirred at room temperature for 13 hours. The reaction mixture was poured into water, and the resulting mixture was extracted with ethyl acetate. The organic layer was washed with water and dried over anhydrous magnesium sulfate, and the solvent was removed under reduced pressure. The residue was purified by column chromatography on silica gel (eluent: dichloromethane/methanol=10/1~5/1) to give 4-[2-(3-acetyloxybenzyloxy)benzyl]-3-(β-D-glucopyranosyloxy)-5-isopropyl-1H-pyrazole. To a solution of 4-[2-(3-acetyloxybenzyloxy)benzyl]-3-(β-D-glucopyranosyloxy)-5-isopropyl-1H-pyrazole (12 mg) in methanol (2 mL) was added sodium methoxide (28% methanol solution, 5 μL), and the mixture was stirred at room temperature for 1 hour. The reaction mixture was concentrated under reduced pressure, and the residue was purified by solid phase extraction on ODS (washing solvent: distilled water, eluent: methanol) to give the title compound (8 mg).

$^1$H-NMR (CD$_3$OD) δ ppm: 1.066 (3H, d, J=6.8 Hz), 1.072 (3H, d, J=6.8 Hz), 2.80–2.95 (1H, m), 3.25–3.45 (4H, m), 3.60–3.70 (1H, m), 3.75–3.90 (3H, m), 5.00–5.15 (3H, m), 6.65–6.75 (1H, m), 6.75–7.00 (4H, m), 7.00–7.20 (3H, m)

EXAMPLE 13

4-(2-Benzyloxybenzyl)-3-(β-D-glucopyranosyloxy)-1-(3-hydroxypropyl)-5-trifluoromethyl-1H-pyrazole The title compound was prepared in a similar manner to that described in Reference Example 19 using 3-bromopropan-1-ol instead of (2-bromoethoxymethyl)benzene.

$^1$H-NMR (CD$_3$OD) δ ppm: 1.95–2.10 (2H, m), 3.25–3.45 (4H, m), 3.61 (2H, t, J=6.1 Hz), 3.65 (1H, dd, J=4.8, 12.2 Hz), 3.80 (1H, dd, J=2.0, 12.2 Hz), 3.90 (2H, s), 4.23 (2H, t, J=7.1 Hz), 5.14 (2H, s), 5.29 (1H, d, J=7.8 Hz), 6.75–6.90 (2H, m), 6.94 (1H, d, J=8.2 Hz), 7.05–7.15 (1H, m), 7.25–7.45 (5H, m)

EXAMPLE 14

4-[2-(3-Bromobenzyloxy)benzyl]-3-(β-D-glucopyranosyloxy)-5-isopropyl-1H-pyrazole The title compound was prepared in a similar manner to that described in Example 11 using 3-(β-D-glucopyranosyloxy)-4-(2-hydroxybenzyl)-5-isopropyl-1H-pyrazole instead of 3-(β-D-glucopyranosyloxy)-4-(2-hydroxybenzyl)-1-(2-hydroxyethyl)-5-trifluoromethyl-1H-pyrazole and using 3-bromobenzyl bromide instead of benzyl bromide.

$^1$H-NMR (CD$_3$OD) δ ppm: 1.00–1.15 (6H, m), 2.80–2.95 (1H, m), 3.25–3.40 (4H, m), 3.60–3.70 (1H,m), 3.75–3.90 (3H, m), 5.05–5.10 (1H, m), 5.13 (2H, s), 6.80–6.90 (1H, m), 6.93 (1H, d, J=8.4 Hz), 7.05–7.15 (2H, m), 7.25–7.35 (1H, m), 7.35–7.50 (2H, m), 7.61 (1H, s)

EXAMPLE 15

4-[2-(3-Chlorobenzyloxy)benzyl]-3-(β-D-glucopyranosyloxy)-5-isopropyl-1H-pyrazole The title compound was prepared in a similar manner to that described in Example 11 using 3-(β-D-glucopyranosyloxy)-4-(2-hydroxybenzyl)-5-isopropyl-1H-pyrazole instead of 3-(β-D-glucopyranosyloxy)-4-(2-hydroxybenzyl)-1-(2-hydroxyethyl)-5-trifluoromethyl-1H-pyrazole and using 3-chlorobenzyl bromide instead of benzyl bromide.

$^1$H-NMR (CD$_3$OD) δ ppm: 1.00–1.15 (6H, m), 2.80–2.95 (1H, m), 3.25–3.40 (4H, m), 3.60–3.70 (1H,m), 3.75–3.90 (3H, m), 5.00–5.10 (1H, m), 5.14 (2H, s), 6.75–6.90 (1H, m), 6.94 (1H, d, J=7.8 Hz), 7.00–7.15 (2H, m), 7.25–7.40 (3H, m), 7.45 (1H, s)

EXAMPLE 16

4-[2-(3-Fluorobenzyloxy)benzyl]-3-(β-D-glucopyranosyloxy)-5-isopropyl-1H-pyrazole The title compound was prepared in a similar manner to that described in Example 11 using 3-(β-D-glucopyranosyloxy)-4-(2-hydroxybenzyl)-5-isopropyl-1H-pyrazole instead of 3-(β-D-glucopyranosyloxy)-4-(2-hydroxybenzyl)-1-(2-hydroxyethyl)-5-trifluoromethyl-1H-pyrazole and using 3-fluorobenzyl bromide instead of benzyl bromide.

$^1$H-NMR (CD$_3$OD) δ ppm: 1.00–1.10 (6H, m), 2.80–2.95 (1H, m), 3.25–3.40 (4H, m), 3.60–3.70 (1H,m), 3.75–3.85 (3H, m), 5.00–5.10 ,1(H, m), 5.15 (2H, s), 6.80–6.90 (1H, m), 6.94 (1H, d, J=7.6 Hz), 7.00–7.20 (4H, m), 7.25 (1H, d, J=7.7 Hz), 7.35–7.45 (1H, m)

EXAMPLE 17

3-(β-D-glucopyranosyloxy)-4-[2-(3-hydroxymethylbenzyloxy)benzyl]-5-isopropyl-1H-pyrazole To a suspension of 3-(β-D-glucopyranosyloxy)-4-(2-hydroxybenzyl)-5-isopropyl-1H-pyrazole (164 mg) and potassium carbonate (115 mg) in N,N-dimethylformamide (5 mL) was added 3-tert-butyldimethylsilyloxymethylbenzyl bromide (197 mg) at room temperature, and the mixture was stirred for 20 hours. The reaction mixture was poured into water, and the resulting mixture was extracted with ethyl acetate. The extract was washed with water and dried over anhydrous magnesium sulfate, and the solvent was removed under reduced pressure. The residue was purified by column chromatography on silica gel (eluent: dichloromethane/methanol=20/1-10/1–5/1) to give 4-[2-(3-tert-butyldimethylsilyloxymethylbenzyloxy)benzyl]-3-(β-D-glucopyranosyloxy)-5-isopropyl-1H-pyrazole. To a solution of the obtained 4-[2-(3-tert-butyldimethylsilyloxymethylbenzyloxy)benzyl]-3-(β-D-glucopyranosyloxy)-5-isopropyl-1H-pyrazole in tetrahydrofuran (2 mL) was added tetra-(n-butyl)ammonium fluoride (1 mol/L tetrahydrofuran solution, 0.065 mL) at room temperature, and the mixture was stirred for 15 hours. The reaction mixture was concentrated under reduced pressure, and the residue was purified by solid phase extraction on ODS (washing solvent: distilled water, eluent: methanol) to give the title compound (22 mg).
$^1$H-NMR (CD$_3$OD) δ ppm: 1.06 (3H, d, J=7.1 Hz), 1.07 (3H, d, J=7.1 Hz), 2.80–2.95 (1H, m), 3.25–3.40 (4H, m), 3.60–3.70 (1H, m), 3.75–3.85 (3H, m), 4.62 (2H, s), 5.00–5.10 (1H, m), 5.13 (2H, s), 6.75–6.85 (1H, m), 6.90–7.00 (1H, m), 7.00–7.15 (2H, m), 7.25–7.40 (3H, m), 7.44 (1H, s)

EXAMPLE 18

5-Ethyl-3-(β-D-glucopyranosyloxy)-4-(2-hydroxybenzyl)-1-(2-hydroxyethyl)-1H-pyrazole The title compound was prepared in a similar manner to that described in Example 6 using 4-(2-benzyloxybenzyl)-1-(2-benzyloxyethyl)-5-ethyl-3-(β-D-glucopyranosyloxy)-1H-pyrazole instead of 4-(2-benzyloxybenzyl)-3-(β-D-glucopyranosyloxy)-5-isopropyl-1H-pyrazole.
$^1$H-NMR (CD$_3$OD) δ ppm: 0.98 (3H, t, J=7.6 Hz), 2.59 (2H, q, J=7.6 Hz), 3.25–3.45 (4H, m), 3.66 (1H, dd, J=5.1, 11.9 Hz), 3.69 (2H, s), 3.75–3.90 (3H, m), 4.01 (2H, t, J=5.5 Hz), 5.05–5.15 (1H, m), 6.65–6.80 (2H, m), 6.90–7.05 (2H, m)

EXAMPLE 19

4-(2-Benzyloxybenzyl)-5-ethyl-3-(β-D-glucopyranosyloxy)-1-(2-hydroxyethyl)-1H-pyrazole The title compound was prepared in a similar manner to that described in Example 11 using 5-ethyl-3-(β-D-glucopyranosyloxy)-4-(2-hydroxybenzyl)-1-(2-hydroxyethyl)-1H-pyrazole instead of 3-(β-D-glucopyranosyloxy)-4-(2-hydroxybenzyl)-1-(2-hydroxyethyl)-5-trifluoromethyl-1H-pyrazole.
$^1$H-NMR (CD$_3$OD) δ ppm: 0.89 (3H, t, J=7.6 Hz), 2.49 (2H, q, J=7.6 Hz), 3.25–3.45 (4H, m), 3.65 (1H, dd, J=5.4, 11.8 Hz), 3.70–3.90 (5H, m), 3.99 (2H, t, J=5.5 Hz), 5.05–5.20 (3H, m), 6.75–6.85 (1H, m), 6.90–7.00 (1H, m), 7.05–7.15 (2H, m), 7.25–7.50 (5H, m)

EXAMPLE 20

4-[2-(2-Fluorobenzyloxy)benzyl]-3-(β-D-glucopyranosyloxy)-5-isopropyl-1H-pyrazole The title compound was prepared in a similar manner to that described in Example 11 using 3-(β-D-glucopyranosyloxy)-4-(2-hydroxybenzyl)-5-isopropyl-1H-pyrazole instead of 3-(β-D-glucopyranosyloxy)-4-(2-hydroxybenzyl)-1-(2-hydroxyethyl)-5-trifluoromethyl-1H-pyrazole and using 2-fluorobenzyl bromide instead of benzyl bromide.
$^1$H-NMR (CD$_3$OD) δ ppm: 1.00–1.10 (6H, m), 2.75–2.90 (1H, m), 3.25–3.45 (4H, m), 3.60–3.70 (1H, m), 3.76 (2H, s), 3.81 (1H, d, J=11.6 Hz), 5.00–5.15 (1H, m), 5.19 (2H, s), 6.75–6.90 (1H, m), 6.99 (1H, d, J=8.2 Hz), 7.00–7.25 (4H, m), 7.30–7.40 (1H, m), 7.45–7.55 (1H, m)

EXAMPLE 21

4-(2-Benzyloxybenzyl)-3-(β-D-glucopyranosyloxy)-5-trifluoromethyl-1H-pyrazole

The title compound was prepared in a similar manner to that described in Example 3 using 4-(2-benzyloxybenzyl)-5-trifluoromethyl-1,2-dihydropyrazol-3-one instead of 4-(2-benzyloxybenzyl)-5-pentafluoroethyl-1,2-dihydropyrazol-3-one.
$^1$H-NMR (CD$_3$OD) δ ppm: 3.25–3.38 (4H, m), 3.62–3.68 (1H, m), 3.77–3.85 (1H, m), 3.88–3.96 (2H,m), 5.14 (2H, s), 5.16–5.22 (1H, m), 6.68–6.97 (3H, m), 7.10–7.15 (1H, m), 7.27–7.45 (5H, m)

EXAMPLE 22

4-(2-Benzyloxybenzyl)-5-ethyl-1,2-dihydropyrazol-3-one

The title compound was prepared in a similar manner to that described in Example 1 using methyl 3-oxopentanoate instead of methyl 4,4-dimethyl-3-oxopentanoate.
$^1$H-NMR (CDCl$_3$) δ ppm: 1.05 (3H, t, J=7.6 Hz), 2.44 (2H, q, J=7.6 Hz), 3.73 (2H, s), 5.11 (2H, s), 6.83–6.93 (2H, m), 7.13–7.17 (2H, m), 7.28–7.48 (5H, m)

EXAMPLE 23

4-(2-Benzyloxybenzyl)-5-methoxymethyl-1,2-dihydropyrazol-3-one

The title compound was prepared in a similar manner to that described in Example 1 using methyl 4-methoxy-3-oxobutylate instead of methyl 4,4-dimethyl-3-oxopentanoate.
$^1$H-NMR (CDCl$_3$) δ ppm: 3.19 (3H, s), 3.74 (2H, s), 4.23 (2H, s), 5.09 (2H, s), 6.86–6.93 (2H, m), 7.12–7.21 (2H, m), 7.28–7.47 (5H, m)

EXAMPLE 24

4-[2-(2-Chlorobenzyloxy)benzyl]-5-trifluoromethyl-1,2-dihydropyrazol-3-one

The title compound was prepared in a similar manner to that described in Example 1 using ethyl 4,4,4-trifluoro-3-oxobutylate instead of methyl 4,4-dimethyl-3-oxopentanoate and using [2-(2-chlorobenzyloxy)phenyl]methanol instead of (2-benzyloxyphenyl)methanol.

$^1$H-NMR (CDCl$_3$) δ ppm: 3.73 (2H, br-s), 5.15 (2H, s), 6.85–7.55 (8H, m)

EXAMPLE 25

4-[2-(3-Chlorobenzyloxy)benzyl]-5-trifluoromethyl-1,2-dihydropyrazol-3-one

The title compound was prepared in a similar manner to that described in Example 1 using ethyl 4,4,4-trifluoro-3-oxobutylate instead of methyl 4,4-dimethyl-3-oxopentanoate and using [2-(3-chlorobenzyloxy)phenyl]methanol instead of (2-benzyloxyphenyl)methanol.

$^1$H-NMR (CDCl$_3$) δ ppm: 3.78 (2H, s), 5.13 (2H, s), 6.85–7.45 (8H, m)

EXAMPLE 26

4-[2-(4-Chlorobenzyloxy)benzyl]-5-trifluoromethyl-1,2-dihydropyrazol-3-one

The title compound was prepared in a similar manner to that described in Example 1 using ethyl 4,4,4-trifluoro-3-oxobutylate instead of methyl 4,4-dimethyl-3-oxopentanoate and using [2-(4-chlorobenzyloxy)phenyl]methanol instead of (2-benzyloxyphenyl)methanol.

$^1$H-NMR (CDCl$_3$) δ ppm: 3.77 (2H, s), 5.15 (2H, s), 6.98–7.03 (2H, m), 7.19–7.28 (2H, m), 7.37–7.44 (4H, m)

EXAMPLE 27

4-(2-Methoxymethoxybenzyl)-5-trifluoromethyl-1,2-dihydropyrazol-3-one

The title compound was prepared in a similar manner to that described in Example 1 using ethyl 4,4,4-trifluoro-3-oxobutylate instead of methyl 4,4-dimethyl-3-oxopentanoate and using (2-methoxymethoxyphenyl)methanol instead of (2-benzyloxyphenyl)methanol.

$^1$H-NMR (CDCl$_3$) δ ppm: 3.51 (3H, s), 3.82 (2H, s), 5.26 (2H, s), 6.90–6.96 (1H, m), 7.04–7.10 (2H, m), 7.13–7.18 (1H, m)

EXAMPLE 28

4-(2-Benzyloxybenzyl)-3-(β-D-glucopyranosyloxy)-5-methoxymethyl-1H-pyrazole

The title compound was prepared in a similar manner to that described in Example 2 using 4-(2-benzyloxybenzyl)-5-methoxymethyl-1,2-dihydropyrazol-3-one instead of 4-(2-benzyloxybenzyl)-5-isopropyl-1,2-dihydropyrazol-3-one.

$^1$H-NMR (CD$_3$OD) δ ppm: 3.12 (3H, s), 3.28–3.40 (4H, m), 3.62–3.67 (1H, m), 3.76–3.83 (3H, m), 4.05–4.13 (2H, m), 5.03–5.10 (1H, m), 5.10 (2H, s), 6.77–6.84 (1H, m), 6.93–6.98 (1H, m), 7.07–7.17 (2H, m), 7.27–7.43 (5H, m)

EXAMPLE 29

4-[2-(2-Chlorobenzyloxy)benzyl]-3-(β-D-glucopyranosyloxy)-5-trifluoromethyl-1H-pyrazole The title compound was prepared in a similar manner to that described in Example 3 using 4-[2-(2-chlorobenzyloxy)benzyl]-5-trifluoromethyl-1,2-dihydropyrazol-3-one instead of 4-(2-benzyloxybenzyl)-5-pentafluoroethyl-1,2-dihydropyrazol-3-one.

$^1$H-NMR (CD$_3$OD) δ ppm: 3.24–3.42 (4H, m), 3.60–3.69 (1H, m), 3.75–3.83 (1H, m), 3.90–4.00 (2H,m), 5.15–5.30 (3H, m), 6.78–6.96 (3H, m), 7.08–7.16 (1H, m), 7.27–7.55 (4H, m)

EXAMPLE 30

4-[2-(3-Chlorobenzyloxy)benzyl]-3-(β-D-glucopyranosyloxy)-5-trifluoromethyl-1H-pyrazole The title compound was prepared in a similar manner to that described in Example 3 using 4-[2-(3-chlorobenzyloxy)benzyl]-5-trifluoromethyl-1,2-dihydropyrazol-3-one instead of 4-(2-benzyloxybenzyl)-5-pentafluoroethyl-1,2-dihydropyrazol-3-one.

$^1$H-NMR (CD$_3$OD) δ ppm: 3.23–3.38 (4H, m), 3.55–3.98 (4H, m), 5.04–5.30 (3H, m), 6.75–6.95 (3H,m), 7.03–7.14 (1H, m), 7.23–7.45 (4H, m)

EXAMPLE 31

4-[2-(4-Chlorobenzyloxy)benzyl]-3-(β-D-glucopyranosyloxy)-5-trifluoromethyl-1H-pyrazole The title compound was prepared in a similar manner to that described in Example 3 using 4-[2-(4-chlorobenzyloxy)benzyl]-5-trifluoromethyl-1,2-dihydropyrazol-3-one instead of 4-(2-benzyloxybenzyl)-5-pentafluoroethyl-1,2-dihydropyrazol-3-one.

$^1$H-NMR (CD$_3$OD) δ ppm: 3.20–3.40 (4H, m), 3.62–3.70 (1H, m), 3.77–3.84 (1H, m), 3.88–3.96 (2H,m), 5.10 (2H, s), 5.10–5.30 (1H, m), 6.77–6.96 (3H, m), 7.07–7.13 (1H, m), 7.32–7.42 (4H, m)

EXAMPLE 32

4-(2-Benzyloxybenzyl)-5-ethyl-3-(β-D-glucopyranosyloxy)-1H-pyrazole

The title compound was prepared in a similar manner to that described in Example 2 using 4-(2-benzyloxybenzyl)-5-ethyl-1,2-dihydropyrazol-3-one instead of 4-(2-benzyloxybenzyl)-5-isopropyl-1,2-dihydropyrazol-3-one.

$^1$H-NMR (CD$_3$OD) δ ppm: 0.97 (3H, t, J=7.6 Hz), 2.38 (2H, q, J=7.6 Hz), 3.25–3.40 (4H, m), 3.61–3.67 (1H, m), 3.75–3.87 (3H, m), 5.02–5.10 (1H, m), 5.12 (2H, s), 6.79–6.86 (1H, m), 6.93–7.00 (1H, m), 7.05–7.15 (2H, m), 7.27–7.47 (5H, m)

EXAMPLE 33

4-(2-Benzyloxybenzyl)-5-pentafluoroethyl-1,2-dihydropyrazol-3-one

The title compound was prepared in a similar manner to that described in Example 1 using ethyl 4,4,5,5,5-pentafluoro-3-oxopentanoate instead of methyl 4,4-dimethyl-3-oxo-pentanoate.

$^1$H-NMR (CDCl$_3$) δ ppm: 3.78 (2H, s), 5.14 (2H, s), 6.90–7.00 (2H, m), 7.14–7.21 (2H, m), 7.32–7.46 (5H, m)

EXAMPLE 34

4-(2-Methoxymethoxybenzyl)-3-(β-D-glucopyranosyloxy)-5-trifluoromethyl-1H-pyrazole The title compound was prepared in a similar manner to that described in Example 3 using 4-(2-methoxymethoxybenzyl)-5-trifluoromethyl-1,2-dihydropyrazol-3-one instead of 4-(2-benzyloxybenzyl)-5-pentafluoroethyl-1,2-dihydropyrazol-3-one.

$^1$H-NMR (CD$_3$OD) δ ppm: 3.27–3.40 (4H, m), 3.42 (3H, s), 3.64–3.72 (1H, m), 3.80–3.93 (3H, m), 5.16–5.30 (3H, m), 6.83–7.14 (4H, m)

EXAMPLE 35

4-(2-Benzyloxybenzyl)-5-tert-butyl-3-(β-D-glucopyranosyloxy)-1H-pyrazole

The title compound was prepared in a similar manner to that described in Example 2 using 4-(2-benzyloxybenzyl)-5-tert-butyl-1,2-dihydropyrazol-3-one instead of 4-(2-benzyloxybenzyl)-5-isopropyl-1,2-dihydropyrazol-3-one.

$^1$H-NMR (CD$_3$OD) δ ppm: 1.19 (9H, s), 3.27–3.35 (3H, m), 3.43–3.47 (1H, m), 3.62–3.67 (1H, m), 3.78–3.83 (1H, m), 3.93 (2H, s), 5.05–5.10 (1H, m), 5.14 (2H, s), 6.75–6.82 (1H, m), 6.84–6.87 (1H, m), 6.95–6.98 (1H, m), 7.06–7.12 (1H, m), 7.27–7.39 (3H, m), 7.43–7.49 (2H, m)

EXAMPLE 36

5-Isopropyl-4-(2-phenoxymethylbenzyl)-1,2-dihydropyrazol-3-one

The title compound was prepared in a similar manner to that described in Example 1 using ethyl 4-methyl-3-oxopentanoate instead of methyl 4,4-dimethyl-3-oxopentanoate and using (2-phenoxymethylphenyl)methanol instead of (2-benzyloxyphenyl)methanol.

$^1$H-NMR (CDCl$_3$) δ ppm: 1.12 (6H, d, J=7.0 Hz), 2.99 (1H, heptet, J=7.0 Hz), 3.81 (2H, s), 5.15 (2H, s), 6.93–7.04 (3H, m), 7.15–7.30 (5H, m), 7.42–7.47 (1H, m)

EXAMPLE 37

5-Isopropyl-4-(2-phenoxybenzyl)-1,2-dihydropyrazol-3-one

The title compound was prepared in a similar manner to that described in Example 1 using ethyl 4-methyl-3-oxopentanoate instead of methyl 4,4-dimethyl-3-oxopentanoate and using (2-phenoxyphenyl)methanol instead of (2-benzyloxyphenyl)methanol.

$^1$H-NMR (CDCl$_3$) δ ppm: 1.12 (6H, d, J=7.0 Hz), 2.93 (1H, heptet, J=7.0 Hz), 3.72 (2H, s), 6.85–7.15 (6H, m), 7.24–7.33 (3H, m)

EXAMPLE 38

5-Isopropyl-4-[2-(2-methylbenzyloxy)benzyl]-1,2-dihydropyrazol-3-one

The title compound was prepared in a similar manner to that described in Example 1 using ethyl 4-methyl-3-oxopentanoate instead of methyl 4,4-dimethyl-3-oxopentanoate and using [2-(2-methylbenzyloxy)phenyl]methanol instead of (2-benzyloxyphenyl)methanol.

$^1$H-NMR (CDCl$_3$) δ ppm: 1.09 (6H, d, J=7.0 Hz), 2.4.0 (3H, s), 2.90 (1H, heptet, J=7.0 Hz), 3.72 (2H, s), 5.09 (2H, s), 6.85–6.96 (2H, m), 7.13–7.30 (5H, m), 7.42–7.45 (1H, m)

EXAMPLE 39

5-Isopropyl-4-[2-(3-methylbenzyloxy)benzyl]-1,2-dihydropyrazol-3-one

The title compound was prepared in a similar manner to that described in Example 1 using ethyl 4-methyl-3-oxopentanoate instead of methyl 4,4-dimethyl-3-oxopentanoate and using [2-(3-methylbenzyloxy)phenyl]methanol instead of (2-benzyloxyphenyl)methanol.

$^1$H-NMR (CDCl$_3$) δ ppm: 1.10 (6H, d, J=7.0 Hz), 2.38 (3H, s), 2.93 (1H, heptet, J=7.0 Hz), 3.75 (2H, s), 5.08 (2H, s), 6.85–6.93 (2H, m), 7.10–7.33 (6H, m)

EXAMPLE 40

5-Isopropyl-4-[2-(3-methoxybenzyloxy)benzyl]-1,2-dihydropyrazol-3-one

The title compound was prepared in a similar manner to that described in Example 1 using ethyl 4-methyl-3-oxopentanoate instead of methyl 4,4-dimethyl-3-oxopentanoate and using [2-(3-methoxybenzyloxy)phenyl]methanol instead of (2-benzyloxyphenyl)methanol.

$^1$H-NMR (CDCl$_3$) δ ppm: 1.11 (6H, d, J=7.0 Hz), 2.95 (1H, heptet, J=7.0 Hz), 3.76 (2H, s), 3.82 (3H, s), 5.10 (2H, s), 6.83–6.92 (3H, m), 7.02–7.04 (2H, m), 7.10–7.16 (2H, m), 7.25–7.30 (1H, m)

EXAMPLE 41

5-Isopropyl-4-[2-(tetrahydropyran-4-yloxy)benzyl]-1,2-dihydropyrazol-3-one

The title compound was prepared in a similar manner to that described in Example 1 using ethyl 4-methyl-3-oxopentanoate instead of methyl 4,4-dimethyl-3-oxopentanoate and using [2-(tetrahydropyran-4-yloxy)phenyl]methanol instead of (2-benzyloxyphenyl)methanol.

$^1$H-NMR (CDCl$_3$) δ ppm: 1.15 (6H, d, J=7.0 Hz), 1.80–1.90 (2H, m), 2.02–2.11 (2H, m), 2.93 (1H, heptet, J=7.0 Hz), 3.57–3.65 (2H, m), 3.69 (2H, s), 3.96–4.03 (2H, m), 4.53–4.60 (1H, m), 6.82–6.88 (2H, m), 7.03–7.14 (2H, m)

EXAMPLE 42

4-[2-(3-Methylbenzyloxy)benzyl]-3-(β-D-glucopyranosyloxy)-5-isopropyl-1H-pyrazole The title compound was prepared in a similar manner to that described in Example 2 using 5-isopropyl-4-[2-(3-methylbenzyloxy)benzyl]-1,2-dihydropyrazol-3-one instead of 4-(2-benzyloxybenzyl)-5-isopropyl-1,2-dihydropyrazol-3-one.

$^1$H-NMR (CD$_3$OD) δ ppm: 1.01–1.10 (6H, m), 2.35 (3H, s), 2.81–2.92 (1H, m), 3.23–3.50 (4H, m), 3.60–3.85 (4H, m), 5.03–5.10 (3H, m), 6.77–6.84 (1H, m), 6.90–7.30 (7H, m)

EXAMPLE 43

3-(β-D-glucopyranosyloxy)-5-isopropyl-4-[2-(3-methoxybenzyloxy)benzyl]-1H-pyrazole The title compound was prepared in a similar manner to that described in Example 2 using 5-isopropyl-4-[2-(3- methoxybenzyloxy)benzyl]-1,2-dihydropyrazol-3-one instead of 4-(2-benzyloxybenzyl)-5-isopropyl-1,2-dihydropyrazol-3-one.

$^1$H-NMR (CD$_3$OD) δ ppm: 0.93–0.98 (6H, m), 2.73–2.82 (1H, m), 3.20–3.30 (4H, m), 3.53–3.60 (2H,m), 3.65–3.73 (5H, m), 4.95–5.03 (3H, m), 6.67–7.01 (7H, m), 7.14–7.21 (1H, m)

EXAMPLE 44

3-(β-D-glucopyranosyloxy)-5-isopropyl-4-[2-(tetrahydropyran-4-yloxy)benzyl]-1H-pyrazole The title compound was prepared in a similar manner to that described in Example 2 using 5-isopropyl-4-[2-(tetrahydropyran-4-yloxy)benzyl]-1,2-dihydropyrazol-3-one instead of 4-(2-benzyloxybenzyl)-5-isopropyl-1,2-dihydropyrazol-3-one.

$^1$H-NMR (CD$_3$OD) δ ppm: 0.96–1.08 (6H, m), 1.63–1.75 (2H, m), 1.88–2.00 (2H, m), 2.72–2.83 (1H,m), 3.17–3.33 (4H, m), 3.43–3.92 (8H, m), 4.46–4.55 (1H, m), 4.92–5.01 (1H, m), 6.67–6.73 (1H, m), 6.82–7.03 (3H, m)

EXAMPLE 45

3-(β-D-glucopyranosyloxy)-5-isopropyl-4-(2-phenoxymethylbenzyl)-1H-pyrazole

The title compound was prepared in a similar manner to that described in Example 2 using 5-isopropyl-4-(2-phenoxymethylbenzyl)-1,2-dihydropyrazol-3-one instead of 4-(2-benzyloxybenzyl)-5-isopropyl-1,2-dihydropyrazol-3-one.

$^1$H-NMR (CD$_3$OD) δ ppm: 1.05–1.15 (6H, m), 2.81–2.90 (1H, m), 3.27–3.40 (4H, m), 3.60–3.66 (1H,m), 3.75–3.93 (3H, m), 5.02–5.20 (3H, m), 6.90–7.04 (3H, m), 7.08–7.31 (5H, m), 7.38–7.43 (1H, m)

EXAMPLE 46

3-(β-D-glucopyranosyloxy)-5-isopropyl-4-(2-phenoxybenzyl)-1H-pyrazole

The title compound was prepared in a similar manner to that described in Example 2 using 5-isopropyl-4-(2-phenoxybenzyl)-1,2-dihydropyrazol-3-one instead of 4-(2-benzyloxybenzyl)-5-isopropyl-1,2-dihydropyrazol-3-one.

$^1$H-NMR (CD$_3$OD) δ ppm: 1.08–1.17 (6H, m), 2.85–2.95 (1H, m), 3.27–3.45 (4H, m), 3.64–3.88 (4H,m), 5.07–5.13 (1H, m), 6.83–6.95 (3H, m), 7.03–7.38 (6H, m)

EXAMPLE 47

4-[2-(2,5-Dimethylbenzyloxy)benzyl]-5-isopropyl-1,2-dihydropyrazol-3-one

The title compound was prepared in a similar manner to that described in Example 1 using ethyl 4-methyl-3-oxopentanoate instead of methyl 4,4-dimethyl-3-oxopentanoate and using [2-(2,5-dimethylbenzyloxy)phenyl]methanol instead of (2-benzyloxyphenyl)methanol.

$^1$H-NMR (CDCl$_3$) δ ppm: 1.07 (6H, d, J=7.0 Hz), 2.33 (3H, s), 2.35 (3H, s), 2.88 (1H, heptet, J=7.0 Hz), 3.72 (2H, s), 5.03 (2H, s), 6.85–6.96 (2H, m), 7.05–7.19 (5H, m)

EXAMPLE 48

4-(2-Benzyloxybenzyl)-5-isopropyl-1,2-dihydropyrazol-3-one

The title compound was prepared in a similar manner to that described in Example 1 using ethyl 4-methyl-3-oxopentanoate instead of methyl 4,4-dimethyl-3-oxopentanoate.

$^1$H-NMR (CDCl$_3$) δ ppm: 1.12 (6H, d, J=7.0 Hz), 2.95 (1H, heptet, J=7.0 Hz), 3.75 (2H, s), 5.13 (2H, s), 6.87–6.94 (2H, m), 7.13–7.17 (2H, m), 7.30–7.47 (5H, m)

EXAMPLE 49

4-(2-Benzyloxybenzyl)-5-trifluoromethyl-1,2-dihydropyrazol-3-one

The title compound was prepared in a similar manner to that described in Example 1 using ethyl 4,4,4-trifluoro-3-oxobutylate instead of methyl 4,4-dimethyl-3-oxopentanoate.

$^1$H-NMR (CDCl$_3$) δ ppm: 3.77 (2H, s), 5.18 (2H, s), 6.98–7.06 (2H, m), 7.21–7.28 (2H, m), 7.39–7.48 (5H, m)

EXAMPLE 50

4-(2-Cycloheptyloxybenzyl)-5-isopropyl-1,2-dihydropyrazol-3-one

The title compound was prepared in a similar manner to that described in Example 1 using ethyl 4-methyl-3-oxobutylate instead of methyl 4,4-dimethyl-3-oxopentanoate and using (2-cycloheptyloxyphenyl)methanol instead of (2-benzyloxyphenyl)methanol.

$^1$H-NMR (CDCl$_3$) δ ppm: 1.18 (6H, d, J=7.0 Hz), 1.40–1.90 (10H, m), 2.00–2.10 (2H, m), 3.01 (1H,heptet, J=7.0 Hz), 3.68 (2H, s), 4.45–4.55 (1H, m), 6.80–6.90 (2H, m), 7.05–7.15 (2H, m)

EXAMPLE 51

4-(2-Cycloheptyloxybenzyl)-3-(β-D-glucopyranosyloxy)-5-isopropyl-1H-pyrazole

The title compound was prepared in a similar manner to that described in Example 5 using 4-(2-cycloheptyloxybenzyl)-5-isopropyl-1,2-dihydropyrazol-3-one instead of 4-[2-(2,5-dimethylbenzyloxy)benzyl]-5-isopropyl-1,2-dihydropyrazol-3-one.

$^1$H-NMR (CD$_3$OD) δ ppm: 0.95–1.10 (6H, m), 1.30–1.80 (10H, m), 1.85–2.00 (2H, m), 2.75–2.85 (1H, m), 3.15–3.35 (4H, m), 3.50–3.75 (4H, m), 4.35–4.45 (1H, m), 4.95–5.00 (1H, m), 6.60–6.80 (2H, m), 6.85–7.05 (2H, m)

TEST EXAMPLE 1

Assay for Inhibitory Effects on Human SGLT1 Activity

1) Cloning and Construction of the Vector Expressing Human SGLT1

The cDNA library was prepared for PCR amplification by reverse transcription from total RNA deprived from human small intestine (Ori gene) using oligo-dT as a primer. Using this cDNA library as a template, the DNA fragment coding 1 to 2005 bp of human SGLT1 (ACCESSION: M24847), which was reported by Hediger et al., was amplified by PCR method and inserted into the multi-cloning site of pcDNA3.1(−) (Invitrogen). The DNA sequence inserted was perfectly matched to the previously reported sequence of human SGLT1.

2) Establishment of Cell Line Stably Expressing Human SGLT1

The expression vector of human SGLT1 was digested by Sca I into a linear DNA. The linear DNA was transfected into CHO-K1 cells by means of lipofection (Effectene Transfection Reagent: QIAGEN). Neomycin resistant cell lines were selected by culture in the medium containing G418 (1 mg/mL, LIFE TECHNOLOGIES), and then the activity against the uptake of methyl-α-D-glucopyranoside was measured by the method described below. The cell line, which showed the greatest uptake activity, was selected and designated as CS1-5-11D. CS1-5–11D cells were cultured in the presence of G418 at 200 μg/mL.

3) Measurement of the Inhibitory Activity Against the Uptake of methyl-α-D-glucopyranoside (α-MG)

CS1-5-11D cells were seeded into a 96-well culture plate at a density of $3 \times 10^4$ cells/well and cultured for 2 days, and were used in the uptake assay. A mixture of non-labeled (Sigma) and $^{14}C$-labeled α-MG (Amersham Pharmcia Biotec) added to the uptake buffer (pH 7.4; containing 140 mM sodium chloride, 2 mM potassium chloride, 1 mM calcium chloride, 1 mM magnesium chloride, 10 mM 2-[4-(2-hydroxyethyl)-1-piperazinyl]ethane sulfonic acid, and 5 mM tris(hydroxymethyl)aminomethane) at the final concentration of 1 mM. A test compound was dissolved in dimethyl sulfoxide, and then appropriately diluted with distilled water. The test compound solution was added to the uptake buffer containing 1 mM α-MG, and designated as a measurement buffer. For the control group, the measurement buffer without any test compound was prepared. For measuring the basal uptake, a basal buffer which contains 140 mM chorine chloride instead of 140 mM sodium chloride was prepared. After removing the culture medium of CS1-5-11D cells, 180 μL of the pre-treatment buffer (the uptake buffer not containing α-MG) was added to each well and incubated at 37° C. for 10 minutes. After repeating the same treatment, the pre-treatment buffer was removed. To each well was added 75 μL of the measurement buffer or the basal buffer was added and incubated at 37° C. for 1 hour. After removing the measurement buffer, cells were washed twice with 180 μL per well of the washing buffer (the basal buffer containing 10 mM non-labeled α-MG). The cells were solubilized by 75 μL per well of 0.2 mol/L sodium hydroxide. The cell lysates were transferred into PicoPlates (Packard), and then added 150 μL of MicroScint-40 (Packard) and mixed. Radioactivity was measured by means of microscintillation counter TopCount (Packard). One hundred % was set to the difference between the uptake in the control group and the basal uptake, and the uptake of methyl α-D-glucopyranoside at each drug concentration were calculated. The drug concentration, at which 50% uptake of methyl α-D-glucopyranoside was inhibited ($IC_{50}$ value), was calculated using logit plot. The results are shown in Table 1.

TABLE 1

| Test compound | $IC_{50}$ value (nM) |
|---|---|
| Example 2 | 18 |
| Example 9 | 8 |
| Example 11 | 13 |
| Example 12 | 35 |

TABLE 1-continued

| Test compound | $IC_{50}$ value (nM) |
|---|---|
| Example 13 | 30 |
| Example 15 | 1 |
| Example 19 | 80 |
| Example 21 | 14 |
| Example 51 | 194 |

TEST EXAMPLE 2

Assay for Inhibitory Effects on Blood Glucose Level Increase in Rats

1) Preparation of Diabetic Rat Model

Ten weeks old rats were injected nicotinamide (230 mg/kg) intraperitoneally. Fifteen minutes after injection, they were injected streptozotocin (65 mg/kg) intravenously from tail vain under anesthesia with ether. Two weeks later, rats were fasted for 5 hours and then oral glucose tolerance test (2 g/kg) was done. The rats which showed plasma glucose concentration at 15 minutes after glucose load was ranged 250–450 mg/dL were selected to use oral liquid meal tolerance test.

2) Liquid Meal Tolerance Test

After 16 hours fasted, the diabetic rats were orally administered a test compound (10 mg/kg), which was suspended with 0.5% sodium carboxymethylcellulose (CMC), in the drug-treating group, or 0.5% sodium carboxymethylcellulose (CMC) alone in a control group. Immediately after the compound administration, 15 kcal/kg of liquid meal (No. 038, Conrol diet, assorted with dextrin and maltose; Oriental Yeast Co., Ltd.) was loaded orally. The blood was collected from tail artery immediately before (0 h), at 0.5 and 1 hour after administration, and treated with heparin immediately. The blood was centrifuged, and the plasma was collected to quantify the plasma glucose concentration. Plasma glucose concentrations at pretreatment (0 h), 0.5 and 1 hour after the drug administration were shown in Table 2. The values in the table are presented as the mean±S.E.

TABLE 2

| Test compound | Plasma glucose concentration (mg/dL) | | |
|---|---|---|---|
| | 0 h | 0.5 h | 1 h |
| Control | 132 ± 7 | 254 ± 16 | 291 ± 21 |
| Example 2 | 126 ± 7 | 194 ± 7 | 219 ± 16 |

TEST EXAMPLE 3

Acute Toxicity Test

Male C57BL/6J mice (CLEA Japan, Inc.; 17 weeks old, 20–23 g, n=5) were fasted for 4 hours. A test compound, which was suspended with 0.5% sodium carboxymethylcellulose, was administered orally at a dose of 1 g/kg, and then mice were observed for 48 hours. The results are shown in the following Table 3.

TABLE 3

| Test compound | Number of death |
|---|---|
| Example 2 | 0/5 |

INDUSTRIAL APPLICABILITY

The glucopyranosyloxypyrazole derivatives represented by the above general formula (I) of the present invention, pharmaceutically acceptable salts thereof and prodrugs thereof exert an inhibitory activity in human SGLT1 and can suppress increase of blood glucose level by inhibiting carbohydrate absorption such as glucose at the small intestine, particularly can normalize postprandial hyperglycemia by delaying carbohydrate absorption based on the mechanism. Therefore, the present invention can provide excellent agents for the prevention or treatment of a disease associated with hyperglycemia such as diabetes, diabetic complications, obesity or the like. In addition, since benzylpyrazole derivatives represented by the above general formula (II) or (III) of the present invention and salts thereof are important as intermediates in the production of the glucopyranosyloxypyrazole derivatives represented by the above general formula (I), the compounds represented the above general formula (I) of the present invention can be readily prepared via such compounds.

What is claimed is:

1. A glucopyranosyloxypyrazole derivative represented by the general formula:

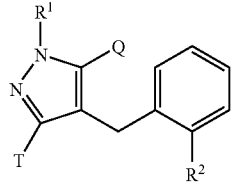

wherein $R^1$ is a hydrogen atom or a hydroxy($C_{2-6}$ alkyl) group; one of Q and T is a group represented by the general formula;

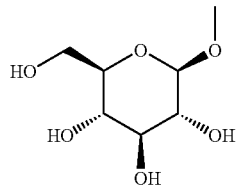

the other is a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group; and $R^2$ is a halogen atom, a hydroxy group, a $C_{1-6}$ alkyl group, a $C_{1-6}$ alkoxy group, a $C_{1-6}$ alkylthio group, a halo($C_{1-6}$ alkyl) group, a halo($C_{1-6}$ alkoxy) group, a $C_{1-6}$ alkoxy-substituted ($C_{1-6}$ alkoxy) group, a $C_{3-7}$ cycloalkyl-substituted ($C_{2-6}$ alkoxy) group, or a group of the general formula: -A-$R^3$ wherein A is a single bond, an oxygen atom, a methylene group, an ethylene group, —OCH$_2$— or —CH$_2$O—; and R$_3$ is a $C_{3-7}$ cycloalkyl group, a $C_{3-7}$ heterocycloalkyl group, an aryl group which may have 1–3 the same or different substituents selected from a halogen atom, a hydroxy group, an amino group, a $C_{1-6}$ alkyl group, a $C_{1-6}$ alkoxy group, a $C_{2-6}$ alkenyloxy group, a halo($C_{1-6}$ alkyl) group, a hydroxy($C_{1-6}$ alkyl) group, a carboxy group, a $C_{2-7}$ alkoxycarbonyl group, a cyano group and a nitro group, a thiazolyl group which may have a substituent selected from a halogen atom and a $C_{1-6}$ alkyl group, or a pyridyl group which may have a substituent selected from a halogen atom and a $C_{1-6}$ alkyl group or a pharmaceutically acceptable salt thereof.

2. A glucopyranosyloxypyrazole derivative as claimed in claim 1, represented by the general formula:

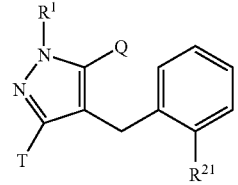

wherein $R^1$ is a hydrogen atom or a hydroxy($C_{2-6}$ alkyl) group; one of Q and T is a group represented by the general formula;

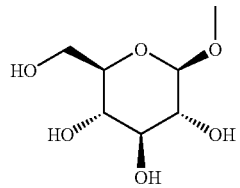

the other is a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group; and $R^{21}$ is a hydroxy group, a halo($C_{1-6}$ alkoxy) group, a $C_{1-6}$ alkoxy-substituted ($C_{1-6}$ alkoxy) group, a $C_{3-7}$ cycloalkyl-substituted ($C_{2-6}$ alkoxy) group, or a group of the general formula: -A-$R^3$ wherein A is a single bond, an oxygen atom, a methylene group, an ethylene group, —OCH$_2$— or —CH$_2$O—; and R$_3$ is a $C_{3-7}$ cycloalkyl group, a $C_{3-7}$ heterocycloalkyl group, an aryl group which may have 1–3 the same or different substituents selected from a halogen atom, a hydroxy group, an amino group, a $C_{1-6}$ alkyl group, a $C_{1-6}$ alkoxy group, a $C_{2-6}$ alkenyloxy group, a halo($C_{1-6}$ alkyl) group, a hydroxy($C_{1-6}$ alkyl) group, a carboxy group, a $C_{2-7}$ alkoxycarbonyl group, a cyano group and a nitro group, a thiazolyl group which may have a substituent selected from a halogen atom and a $C_{1-6}$ alkyl group, or a pyridyl group which may have a substituent selected from a halogen atom and a $C_{1-6}$ alkyl group or a pharmaceutically acceptable salt thereof.

3. A glucopyranosyloxypyrazole derivative as claimed in claim 2, represented by the general formula:

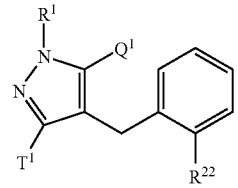

wherein $R^1$ is a hydrogen atom or a hydroxy($C_{2-6}$ alkyl) group; one of $Q^1$ and $T^1$ is a group represented by the general formula;

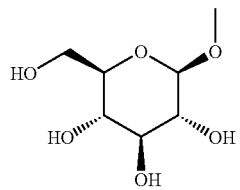

the other is a $C_{1-6}$ alkyl group or a halo($C_{1-6}$ alkyl) group; and $R^{22}$ is a group of the general formula: -A-$R^{31}$ wherein A is a single bond, an oxygen atom, a methylene group, an ethylene group, —OCH$_2$— or —CH$_2$O—; and $R^{31}$ is an aryl group which may have 1–3 the same or different substituents selected from a halogen atom, a hydroxy group, an amino group, a $C_{1-6}$ alkyl group, a $C_{1-6}$ alkoxy group, a $C_{2-6}$ alkenyloxy group, a halo($C_{1-6}$ alkyl) group, a hydroxy($C_{1-6}$ alkyl) group, a carboxy group, a $C_{2-7}$ alkoxycarbonyl group, a cyano group and a nitro group or a pharmaceutically acceptable salt thereof.

4. A pharmaceutical composition comprising as an active ingredient a glucopyranosyloxypyrazole derivative as claimed in any one of claims 1–3 or a pharmaceutically acceptable salt thereof.

5. A method for the treatment of a disease associated with hyperglycemia, which comprises administering to a patient in need of said treatment an effective amount of a glucopyranosyloxypyrazole derivative as claimed in any one of claims 1–3, or a pharmaceutically acceptable salt thereof.

* * * * *